United States Patent [19]

Hashimoto et al.

[11] Patent Number: 4,497,801

[45] Date of Patent: Feb. 5, 1985

[54] NEW PEPTIDES, PROCESS FOR PREPARATION THEREOF AND USE THEREOF

[75] Inventors: Masashi Hashimoto, Takarazuka; Keiji Hemmi, Suita; Daijiro Hagiwara, Moriguchi, all of Japan

[73] Assignee: Fujisawa Pharmaceutical Co., Ltd., Osaka, Japan

[21] Appl. No.: 529,646

[22] Filed: Sep. 6, 1983

[30] Foreign Application Priority Data

Sep. 17, 1982 [JP] Japan .................................. 57-162873
Nov. 25, 1982 [JP] Japan .................................. 57-207335

[51] Int. Cl.³ ..................... A61K 37/00; C07C 103/52
[52] U.S. Cl. ............................... 514/15; 260/112.5 R; 514/18
[58] Field of Search .................. 260/112.5 R; 424/177

[56] References Cited

U.S. PATENT DOCUMENTS

| 4,002,602 | 1/1977 | Goldstein | 260/112.5 R |
| 4,116,951 | 9/1978 | Wang | 424/177 |
| 4,148,788 | 4/1979 | Wang | 424/177 |
| 4,167,557 | 9/1979 | Goldstein | 260/112.5 R |
| 4,229,438 | 10/1980 | Fujino et al. | 260/112.5 R |
| 4,297,276 | 10/1981 | Goldstein et al. | 260/112.5 R |
| 4,353,821 | 10/1982 | Beir et al. | 260/112.5 R |
| 4,404,133 | 9/1983 | Yanaihara et al. | 260/112.5 R |

OTHER PUBLICATIONS

G. Goldstein, Biochemistry 14, 2214–2218 (1975).
AL, Goldstein, Proceedings of National Academy of Science, USA, 74, 725–729 (1977); and 78, 1162–1166 (1981).
J. M. Back, The Journal of Biochemical Chemistry, 250, 1490–1512 (1975), 252, 8045–8047 (1977).
G. Goldstein, Cell, 5, 361–365 (1975).

*Primary Examiner*—Delbert R. Phillips
*Attorney, Agent, or Firm*—Oblon, Fisher, Spivak, McClelland & Maier

[57] ABSTRACT

Peptides of the following formulae:
H-THR-LYS-GLU-LYS-LEU-LYS-SER-GLU-LEU-VAL-ALA-ASN-OH,
H-GLU-LEU-LYS-SER-GLU-LEU-VAL-ALA-ASN-OH, H-LYS-LEU-LYS-SER-GLU-OH, are effective in the treatment of bacteria viral infection.

4 Claims, No Drawings

NEW PEPTIDES, PROCESS FOR PREPARATION THEREOF AND USE THEREOF

This invention relates to new peptides. More particularly, this invention relates to new peptides and their pharmaceutically acceptable salts which have immunomodulating activities, to processes for preparation thereof and to a pharmaceutical composition comprising the same and a method of use thereof.

As a technological background of this invention, thymosins, thymopoietins, concanavalin A, uniquitin and serum thymic factor are known as natural peptides possessing immunomodulating activities, which are described, for example, in Proceedings of National Academy of Science, USA, 74, 725 (1977), and 78, 1162 (1981); Cell, 5, 361 (1975); Journal of Biological Chemistry, 250, (4), 1490–1503 (1975) and 252, 8045 (1977); and Biochemistry, 14, 2214 (1975).

These natural peptides, however, are not satisfactory for industrial manufacture because of their long chain-peptides of amino acids.

The inventors of this invention, as a result of extensive study, have succeeded in preparing certain fragments of said natural peptides, i.e., the new peptides of this invention, which have been found to possess strong immunopotentiating activities.

Accordingly, one object of this invention is to provide new peptides which are relatively short chain-peptides of amino acids, possessing strong immunopotentiating activities, as compared with the afore-mentioned natural peptides.

Another object of this invention is to provide processes for preparation of the new peptides.

Further object of this invention is to provide a pharmaceutical composition comprising the new peptides and a method of use of the new peptides for treating infectious diseases caused by pathogenic microorganisms or virus.

The new peptides of this invention can be represented by the following formulae (I-XVI).

H-Thr-Lys-Asp-Leu-Lys-Glu-Lys-Lys-Glu-Val-Val-Glu-Glu-OH (I)

H-Asp-Leu-Lys-Glu-Lys-Lys-Glu-Val-Val-Glu-Glu-OH (II)

H-Lys-Glu-Lys-Lys-Glu-OH (III)

H-Lys-Ser-Lys-Leu-Lys-Lys-Thr-Glu-Thr-Gln-Glu-OH (IV)

H-Lys-Phe-Asp-Lys-Ser-Lys-Leu-Lys-Lys-Thr-Glu-Thr-Gln-Glu-OH (V)

H-Thr-Lys-Glu-Lys-Leu-Lys-Ser-Glu-Leu-Val-Ala-Asn-OH (VI)

H-Glu-Lys-Leu-Lys-Ser-Glu-Leu-Val-Ala-Asn-OH (VII)

H-Lys-Leu-Lys-Ser-Glu-OH (VIII)

H-Ile-Lys-Ser-Val-Arg-Ser-Lys-Lys-Thr-Ala-Lys-Trp-Asn-OH (IX)

H-Ser-Val-Arg-Ser-Lys-Lys-Thr-Ala-Lys-Trp-Asn-OH (X)

H-Ser-Lys-Leu-Lys-Ser-Asn-Ser-Thr-His-Gln-OH (XI)

H-Tyr-Asn-Ser-Val-Asp-Lys-Arg-OH (XII)

H-Asn-Val-Lys-Ala-Lys-Ile-Gln-Asp-Lys-Glu-Gly-OH (XIII)

H-Lys-Glu-Thr-Ile-Glu-Gln-Glu-Lys-Gln-OH (XIV)

H-Glu-Gln-Glu-Lys-Gln-OH (XV)

R-Gln-Gly-Gly-Ser-Asn-OH (XVI)

(wherein R is pGlu-Lys-Ala-Lys-Ser-, pGlu-Lys-Ala-Lys-Lys- or pGlu-Ala-Lys-Lys-).

In this specification, amino acids, protective groups, active groups, solvents, etc. are sometimes designated either by the abbreviations adopted by IUPAC-IUB commission on Biological Nomenclature or by those commonly used in the art. Some of such abbreviations are as follows. Asn: asparagine, Asp: aspartic acid, Ser: serine, Gly: glycine, Glu: glutamic acid, Gln: glutamine, Lys: lysine, Ala: alanine, Thr: threonine, Leu: leucine, Val: valine, pGlu: pyrroglutamic acid, Phe: phenylalanine, Ile: isoleucine, Arg: arginine, Trp: tryptophan, His: histidine, Tyr: tyrosine, Boc: t-butoxycarbonyl, z: benzyloxycarbonyl, Cl-z: 2-chlorobenzyloxycarbonyl, Bzl: benzyl, OBzl: benzyl ester, Tos: p-toluenesulfonyl, CHO: formyl, $Cl_2Bzl$: 2,6-dichlorobenzyl ester, $NO_2$: nitro, opac: phenacyl ester.

New, peptides (I-XVI) and their pharmaceutically acceptable salts according to this invention can be produced by the following procedures.

(1) Process 1

(peptide synthesis by the solid phase method)

(1)-1:
$R^1$-Glu($OR^2$)-resin→$R^1$-Thr($R^3$)-Lys($R^1$)-Asp($OR^2$)-Leu-Lys($R^1$)-Glu($OR^2$)-Lys($R^1$)-Lys($R^1$)-Glu($OR^2$)-Val-Val-Glu($OR^2$)-Glu($OR^2$)-resin($I^a$)

(1)-2:
$R^1$-Glu($OR^2$)→$R^1$-Asp($OR^2$)-Leu-Lys($R^1$)-Glu($OR^2$)-Lys($R^1$)-Lys($R^1$)-Glu($OR^2$)-Val-Val-Glu($OR^2$)-Glu($OR^2$)-resin ($II^a$)

(1)-3:
$R^1$-Glu($OR^2$)-resin→$R^1$-Lys($R^1$)-Ser($R^3$)-Lys($R^1$)-Leu-Lys($R^1$)-Lys($R^1$)-Thr($R^3$)-Glu($OR^2$)-Thr($R^3$)-Gln-Glu($OR^2$)-resin ($IV^a$)

(1)-4:
$R^1$-Glu($OR^2$)-resin→$R^1$-Lys($R^1$)-Phe-Asp($OR^2$)-Lys($R^1$)-Ser($R^3$)-Lys($R^1$)-Leu-Lys($R^1$)-Lys($R^1$)-Thr($R^3$)-Glu($OR^2$)-Thr($R^3$)-Gln-Glu($OR^2$)-resin ($V^a$)

(1)-5:
Resin→$R^1$-Thr($R^3$)-Lys($R^1$)-Glu($OR^2$)-Lys($R^1$)-Leu-Lys($R^1$)-Ser-($R^3$)-Glu($OR^2$)-Leu-Val-Ala-Asp(resin)$OR^2$ ($VI^a$)

(1)-6:
Resin→$R^1$-Glu($OR^2$)-Lys($R^1$)-Leu-Lys($R^1$)-Ser($R^3$)-Glu($OR^2$)-Leu-Val-Ala-Asp(resin)$OR^2$ ($VII^a$)

(1)-7:
Resin→$R^1$-Ile-Lys($R^1$)-Ser($R^3$)-Val-Arg($R^4$)-Ser($R^3$)-Lys($R^1$)-Lys($R^1$)-Thr($R^3$)-Ala-Lys($R^1$)-Trp($R^1$)-Asp(resin)$OR^2$ ($IX^a$)

(1)-8:
Resin→$R^1$-Ser($R^3$)-Val-Arg($R^4$)-Ser($R^3$)-Lys($R^1$)-Lys($R^1$)-Thr($R^3$)-Ala-Lys($R^1$)-Trp($R^1$)-Asp(resin)$OR^2$ ($X^a$)

(1)-9:
Resin→$R^1$-Ser($R^3$)-Lys($R^1$)-Leu-Lys($R^1$)-Ser($R^3$)-Asn-Ser($R^3$)-Thr($R^3$)-His($R^1$)-Glu(resin)$OR^2$ ($XI^a$)

(1)-10:

R$^1$-Gly-resin→R$^1$-Asn-Val-Lys(R$^1$)-Ala-Lys(R$^1$)-Ile-Gln-Asp(OR$^2$)-Lys(R$^1$)-Glu(OR$^2$)-Gly-resin (XIII$^a$)

(1)-11:
Resin→R$^1$-Lys(R$^1$)-Glu(OR$^2$)-Thr(R$^3$)-Ile-Glu(OR$^2$)-Gln-Glu(OR$^2$)-Lys(R$^1$)-Glu(resin)OR$^2$ (XIV$^a$)

(1)-12:
Resin→R$^1$-Glu(OR$^2$)-Gln-Glu(OR$^2$)-Lys(R$^1$)-Glu(resin)OR$^2$ (XV$^a$)

(1)-13:
Resin→R$^a$-Gln-Gly-Gly-Ser(R$^3$)-Asp(resin)OR$^2$ (XVI$^a$) [wherein R$^a$ is R$^1$-pGlu-Lys(R$^1$)-Ala-Lys(R$^1$)-Ser(R$^3$), R$^1$-pGlu-Lys(R$^1$)-Ala-Lys(R$^1$)-Lys(R$^1$) or R$^1$-pGlu-Ala-Lys(R$^1$)-Lys(R$^1$)].

(2) Process 2
(Peptide synthesis by solution method)

(2)-1:
H-Glu(OR$^2$)-Lys(R$^1$)-Lys(R$^1$)-Glu(OR$^2$)-OR$^2$(III-1) R$^1$-Lys(R$^1$)-OH(III-2), R$^1$-Lys(R$^1$)-Glu(OR$^2$)-Lys(R$^1$)-Lys(R$^1$)-Glu(OR$^2$)OR$^2$ (III$^a$)

(2)-2:
H-Leu-Lys(R$^1$)-Ser(R$^3$)-Glu(OR$^2$)-OR$^2$ (VIII-1) R$^1$-Lys(R$^1$)-OH(III-2) R$^1$-Lys(R$^1$)-Leu-Lys(R$^1$)-Ser(R$^3$)-Glu(OR$^2$) OR$^2$ (VIII$^a$)

(2)-3:
R$^1$-Tyr(R$^3$)-Asn-Ser(R$^3$)-OH(XII-1)+H-Val-Asp(OR$^2$)-Lys(R$^1$)-Arg(R$^4$)OR$^2$ (XII-2)→R$^1$-Tyr(R$^3$)-Asn-Ser(R$^3$)-Val-Asp(OR$^2$)-Lys(R$^1$)-Arg(R$^4$)OR$^2$ (XII$^a$)

(3) Process 3
(Elimination of protective groups):

(3)-1:
R$^1$-Thr(R$^3$)-Lys(R$^1$)-Asp(OR$^2$)-Leu-Lys(R$^1$)-Glu(OR$^2$)-Lys(R$^1$)-Lys(R$^1$)-Glu(OR$^2$)-Val-Val-Glu(OR$^2$)-Glu(OR$^2$)-resin(I$^a$)→H-Thr-Lys-Asp-Leu-Lys-Glu-Lys-Lys-Glu-Val-Val-Glu-Glu-OH (I)

(3)-2:
R$^1$-Asp(OR$^2$)-Leu-Lys(R$^1$)-Glu(OR$^2$)-Lys(R$^1$)-Lys(R$^1$)-Glu(OR$^2$)-Val-Val-Glu(OR$^2$)-Glu(OR$^2$)-resin (II$^a$)→H-Asp-Leu-Lys-Glu-Lys-Lys-Glu-Val-Val-Glu-Glu-OH (II)

(3)-3:
R$^1$-Lys(R$^1$)-Glu(OR$^2$)-Lys(R$^1$)-Lys(R$^1$)-Glu(OR$^2$)OR$^2$ (III$^a$)→H-Lys-Glu-Lys-Lys-Glu-OH (III)

(3)-4:
R$^1$-Lys(R$^1$)-Ser(R$^3$)-Lys(R$^1$)-Leu-Lys(R$^1$)-Lys(R$^1$)-Thr(R$^3$)-Glu(OR$^2$)-Thr(R$^3$)-Gln-Glu(OR$^2$)-resin (IV$^a$)→H-Lys-Ser-Lys-Leu-Lys-Lys-Thr-Glu-Thr-Gln-Glu-OH (IV)

(3)-5:
R$^1$-Lys(R$^1$)-Phe-Asp(OR$^2$)-Lys(R$^1$)-Ser(R$^3$)-Lys(R$^1$)-Leu-Lys(R$^1$)-Lys(R$^1$)-Thr(R$^3$)-Glu(OR$^2$)-Thr(R$^3$)-Gln-Glu(OR$^2$)-resin (V$^a$)→H-Lys-Phe-Asp-Lys-Ser-Lys-Leu Lys-Lys-Thr-Glu-Thr-Gln-Glu-OH (V)

(3)-6:
R$^1$-Thr(R$^3$)-Lys(R$^1$)-Glu(OR$^2$)-Lys(R$^1$)-Leu-Lys(R$^1$)-Ser-(R$^3$)-Glu(OR$^2$)-Leu-Val-Ala-Asp(resin)OR$^2$ (VI$^a$)→H-Thr-Lys-Glu-Lys-Leu-Lys-Ser-Glu-Leu-Val-Ala-Asn-OH (VI)

(3)-7:
R$^1$-Glu(OR$^2$)-Lys(R$^1$)-Leu-Lys(R$^1$)-Ser(R$^3$)-Glu(OR$^2$)-Leu-Val-Ala-Asp(resin)OR$^2$ (VII$^a$)→H-Glu-Lys-Leu-Lys-Ser-Glu-Leu-Val-Ala-Asn-OH (VII)

(3)-8:
R$^1$-Lys(R$^1$)-Leu-Lys(R$^1$)-Ser(R$^3$)-Glu(OR$^2$)OR$^2$ (VIII$^a$)→H-Lys-Leu-Lys-Ser-Glu-OH (VIII)

(3)-9
R$^1$-Ile-Lys(R$^1$)-Ser(R$^3$)-Val-Arg(R$^4$)-Ser(R$^3$)-Lys(R$^1$)-Lys(R$^1$)-Thr(R$^3$)-Ala-Lys(R$^1$)-Trp(R$^1$)-Asp(resin)OR$^2$ (IX$^a$)→H-Ile-Lys-Ser-Val-Arg-Ser-Lys-Lys-Thr-Ala-Lys-Trp-Asn-OH (IX)

(3)-10:
R$^1$-Ser(R$^3$)-Val-Arg(R$^1$)-Ser(R$^3$)-Lys(R$^1$)-Lys(R$^1$)-Thr(R$^3$)-Ala-Lys(R$^1$)-Trp(R$^1$)-Asp(resin)OR$^2$(X$^a$)→H-Ser-Val-Arg-Ser-Lys-Lys-Thr-Ala-Lys-Trp-Asn-OH (X)

(3)-11:
R$^1$-Ser(R$^3$)-Lys(R$^1$)-Leu-Lys(R$^1$)-Ser(R$^3$)-Asn-Ser(R$^3$)-Thr(R$^3$)-His(R$^1$)-Glu(resin)OR$^2$(XI$^a$)→H-Ser-Lys-Leu-Lys-Ser-Asn-Ser-Thr-His-Gln-OH (XI)

(3)-12:
R$^1$-Tyr(R$^3$)-Asn-Ser(R$^3$)-Val-Asp(OR$^2$)-Lys(R$^1$)-Arg(R$^4$)OR$^2$(XII$^a$)→H-Tyr-Asn-Ser-Val-Asp-Lys-Arg-OH (XII)

(3)-13:
R$^1$-Asn-Val-Lys(R$^1$)-Ala-Lys(R$^1$)-Ile-Gln-Asp(OR$^2$)-Lys(R$^1$)-Glu(OR$^2$)-Gly-resin (XIII$^a$)→H-Asn-Val-Lys-Ala-Lys-Ile-Gln-Asp-Lys-Glu-Gly-OH (XIII)

(3)-14:
R$^1$-Lys(R$^1$)-Glu(OR$^2$)-Thr(R$^3$)-Ile-Glu(OR$^2$)-Gln-Glu(OR$^2$)-Lys(R$^1$)-Glu(resin)OR$^2$ (XIV$^a$)→H-Lys-Glu-Thr-Ile-Glu-Gln-Glu-Lys-Gln-OH (XIV)

(3)-15:
R$^1$-Glu(OR$^2$)-Gln-Glu(OR$^2$)-Lys(R$^1$)-Glu(resin)-OR$^2$ (XV$^a$)→H-Glu-Gln-Glu-Lys-Gln-OH (XV)

(3)-16:
R$^a$-Gln-Gly-Gly-Ser(R$^3$)-Asp(resin)OR$^2$ (XVI$^a$)→R-Gln-Gly-Gly-Ser-Asn-OH (XVI)

[wherein R and R$^a$ have each the same meaning as defined hereinbefore.]

In the above formulas, R$^1$ means an amino-protecting group, R$^2$ a carboxy-protecting group, R$^3$ a hydroxy-protecting group, and R$^4$ a guanidino-protecting group.

The above definitions will be further explained below.

(1) Amino-protecting group R$^1$

The amino-protecting group is exemplified by the common amino-protecting groups generally employed in the field of amino acid and peptide chemistry and includes such preferred groups as alkoxycarbonyl and cycloalkoxycarbonyl groups (e.g. t-butoxycarbonyl, t-pentoxycarbonyl, cyclohexyloxycarbonyl, etc.), aralkyloxycarbonyl groups such as substituted or unsubstituted phenyl-lower alkoxycarbonyl (e.g. benzyloxycarbonyl, 2-chlorobenzyloxycarbonyl, etc.), substituted or unsubstituted arenesulfonyl groups (e.g. benzenesulfonyl, p-toluenesulfonyl, etc.), alkanoyl groups (e.g. formyl, acetyl, etc.) and so on.

(2) Carboxy-protecting group R$^2$

The carboxy-protecting group is exemplified by the common carboxy-protecting groups generally employed in the field of amino acid and peptide chemistry, and includes such preferred groups as lower alkyl groups (e.g. methyl, ethyl, etc.), cycloalkyl groups (e.g. cyclopentyl, cyclohexyl, etc.), aralkyl groups such as mono- or diphenyl-lower alkyl groups (e.g. benzyl, diphenylmethyl, etc.), aroylalkyl groups (e.g. phenacyl, toluoylethyl, etc.) and so on.

(3) Hydroxy-protecting group R$^3$

The hydroxy-protecting group is exemplified by the common hydroxy-protecting groups generally employed in the field of amino acid and peptide chemistry. Preferred examples of such hydroxy-protecting groups include acyl groups such as alkanoyl groups (e.g. acetyl etc.) and substituted or unsubstituted aralkyl groups (e.g. benzyl, 2,6-dichlorobenzyl, etc.).

(4) Guanidino-protecting group $R^4$

The guanidino-protecting group is exemplified by the common guanidino-protecting groups generally employed in the field of amino acid and peptide chemistry. Preferred examples of such protective groups include nitro, substituted or unsubstituted arenesulfonyl groups (e.g. p-toluenesulfonyl, etc.), substituted or unsubstituted phenyl-lower alkoxycarbonyl groups (e.g. benzyloxycarbonyl, etc.) and so on.

(5) Pharmaceutically acceptable salt

The pharmaceutically acceptable salt, with reference to compounds (I) through (XVI) includes salts with inorganic or organic bases such as alkali metal salts (e.g. sodium salt, potassium salt, etc.), alkaline earth metal salts (e.g. calcium salt, etc.), ammonium salts, organic amine salts (e.g. ethanolamine salt, triethylamine salt, dicyclohexylamine salt, etc.), etc. and organic acid or inorganic acid addition salts such as those with trifluoroacetic acid, methanesulfonic acid, hydrochloric acid, sulfuric acid, nitric acid, phosphoric acid, etc., among others.

Each of the above-mentioned production processes will now be described in detail.

(1) Process 1 (peptide synthesis by solid phase method) [(1)-1 through 13]:

In this process, protected constituent amino acids are sequentially coupled in the conventional manner of peptide synthesis by the solid phase technique to give compounds $I^a$, $II^a$, $IV^a$, $V^a$, $VI^a$, $VII^a$, $IX^a$, $X^a$, $XI^a$, $XIII^a$, $XIV^a$, $XV^a$ and $XVI^a$.

The resin used in this process may be one of those commonly employed in solid-phase peptide synthesis and, thus, includes polystyrene resins such as chloromethylated styrene-divinylbenzene copolymer, hydroxymethylated styrene-divinylbenzene copolymer, aminomethylated styrene-divinylbenzene copolymer, benzylaminated styrene-divinylbenzene copolymer (benzhydrylamine resin), etc., and polyamide resins such as polydimethylacrylamide resin, etc. to name but a few.

The starting material used in this solid-phase peptide synthesizing process, $R^1$-Glu(resin)$OR^2$, includes the known substances (Refer, for example, to Archives of Biochemistry and Biophysics 199, NO. 1, p.286, 1980) as well as novel substances which can be prepared by procedures analogous to those described in the literature just mentioned. The starting material $R^1$-Gly-resin also includes the known substances [Helvetica Chimica Acta 56, 1476 (1973)] as well as novel substances which can be prepared by procedures similar to those set forth in the literature cited just above.

This process is generally conducted with the following steps 1 through 11 as a cycle for each of the protected amino acids.

(1) Step 1:

This step comprises washing the starting material resin or protected amino acid-resin or swelling the resin. Regarding the solvent used for this step, preferred examples include methylene chloride, chloroform and dimethylformamide as well as mixtures thereof.

(2) Step 2:

This step comprises removing the amino-protecting group from the protected amino acid-resin. The reaction in this step is carried out substantially in the same manner as process 3-1 which appears hereinafter.

(3) Step 3:

This step comprises removing impurities and swelling the resin, and is carried out substantially in the same manner as Step 1 described above.

(4) Step 4:

This step is intended to shrink the resin for an improved washing effect. Treatment of the amino acid-resin with alcohol (e.g. methanol, ethanol, propanol, 2-propanol, butanol, etc.), dioxane or the like is a preferred procedure.

(5) Step 5:

This step comprises removing impurities and swelling the resin, and is carried out substantially in the same manner as Step 1 described hereabove.

(6) Step 6:

This is a desalting procedure which is carried out when the amino acid in the amino acid-resin obtained by Steps (1) through (5) exists as an acid addition salt at the α-amino function. For example, this step comprises treating the amino acid-resin with a base such as triethylamine or the like.

(7) Step 7:

This step is intended to remove impurities and swell the resin, and is carried out substantially in the same manner as step 1 described hereabove.

(8) Step 8:

This step comprises coupling the protected component amino acids. It can be carried out in a solvent such as methylene chloride, chloroform, dimethylformamide or the like in the presence of an ordinary condensing agent such as dicyclohexylcarbodiimide, or in the above-mentioned solvent after activating the carboxy group of each protected amino acid into an acid anhydride, active ester or the like in the conventional manner.

(9) Step 9:

This step is intended to remove impurities and swell the resin, and is carried out substantially in the same manner as step 1 described hereabove.

(10) Step 10:

This step is intended to shrink the resin for an improved washing effect, and is carried out substantially in the same manner as step 4 set forth above.

(11) Step 11:

This is a step for washing and swelling the resin and is carried out substantially in the same manner as step 1 described hereabove.

The above-mentioned steps are each carried out generally in the neighborhood of room temperature, and with the exception of step 8, each step is preferably carried out repeatedly, i.e. twice or 3 times.

(2) Process 2 (peptide synthesis by solution method) [(2)-1 through 3]:

This process actually consists of the process [(2)-1] which comprises reacting compound (III-1) or a salt thereof with compound (III-2) or a salt thereof to give compound ($III^a$) or a salt thereof; the process [(2)-2] which comprises reacting compound (VIII-1) or a salt thereof with compound (III-2) or a salt thereof to give compound ($VIII^a$) or a salt thereof; and the process [(2)-3] which comprises reacting compound (XII-1) or a salt thereof with compound (XII-2) or a salt thereof to give compound ($XII^a$) or a salt thereof, all of said processes being conducted by the conventional solution method.

The starting compounds (III-1), (VIII-1), (XII-1), and (XII-2) for this process are all novel compounds, which can be produced by the procedures set forth hereinafter as production examples or by procedures analogous thereto.

The reactions in this process are carried out as follows. In one of the procedures, the carboxy group of compound (III-2) or compound (XII-1) or a salt of either compound is activated in the conventional manner to give an acid halide, acid azide, acid anhydride, mixed acid anhydride, active ester, or the like and this activation product compound is then reacted with compound (III-1), compound (VIII-1) and compound (XII-2) to give compounds (III$^a$), (VIII$^a$) and (XII$^a$), respectively. Another procedure comprises reacting compound (III-1) or a salt thereof with compound (III-2) or a salt thereof, compound (VIII-1) or a salt thereof and compound (IV-2) or a salt thereof, and compound (XII-1) or a salt thereof with compound (XII-2) or a salt thereof, all directly and in the presence of the common condensing agent such as N,N-dicyclohexylcarbodiimide or the like.

Referring to the activation techniques, the most desirable procedure or/and condensing agent are selected with reference to the kind of carboxy-protecting group and the reaction conditions chosen (e.g. reaction solvent, reaction temperature, etc.).

The reaction proceeds smoothly in a solvent such as methylene chloride, chloroform, tetrahydrofuran, dioxane, ethyl acetate, methanol, ethanol, water or the like under cooling (e.g. −20° C.) or at room temperature. The reaction in the presence of a condensing agent is generally carried out under anhydrous and mild conditions.

(3) Process 3 (for removal of protective groups) [(3)-1 through 16]:

This is a process which comprises eliminating the amino-protecting, guanidino-protecting, carboxy-protecting and hydroxy-protecting groups from compounds (I$^a$) through (XVI$^a$) or salts thereof to give compounds (I) through (XVI) or salts thereof.

Since the resin bound to the peptide can be regarded as an amino-protecting or carboxy-protecting group, the description concerning amino-protecting and carboxy-protecting groups should be construed as referring also to the resin.

The reactions for eliminating such amino-, guanidino-, carboxy- and hydroxy-protecting groups are carried out in the conventional manner, i.e. either stepwise or simultaneously, as described hereinbelow.

(1) Process 3-1:

Elimination of amino-protecting and guanidino-protecting groups:

This reaction is conducted in the per se conventional manner, for example by catalytic reduction, the liquid ammonia-alkali metal method, the method utilizing an acid, the acid-zinc method, the method using a base, the hydrazine method, or the like.

Of the above-mentioned techniques, the method using an acid is the commonest technique and will therefore be explained in detail.

This reaction is conducted in a solvent such as methylene chloride, chloroform, acetic acid or water in the presence of an inorganic acid or organic acid such as trifluoroacetic acid, formic acid, p-toluenesulfonic acid, hydrochloric acid, hydrobromic acid, etc. and preferably with the addition of anisole or the like.

Among the above-illustrated acids, trifluoroacetic acid and formic acid can also be used as solvents.

This reaction is generally conducted under cooling (e.g. −78° C.) or at room temperature.

(2) Process 3-2:

Elimination of carboxy-and-hydroxy-protecting groups:

(i) Hydrolysis:

This hydrolysis reaction is preferably conducted in the presence of an acid or a base.

Preferred examples of the acid include inorganic acids (e.g. hydrochloric acid, hydrobromic acid, sulfuric acid, etc.), organic acids (e.g. formic acid, acetic acid, trifluoroacetic acid, propionic acid, benzenesulfonic acid, p-toluenesulfonic acid, etc.), and acidic ion exchange resins.

Preferred examples of the base include inorganic bases such as the hydroxides, carbonates or bicarbonates of alkali metals or alkaline earth metals (e.g. sodium hydroxide, potassium hydroxide, sodium carbonate, potassium carbonate, lithium carbonate, sodium hydrogen carbonate, calcium hydroxide, magnesium hydroxide, etc.), ammonium hydroxide, etc., among others.

The hydrolysis reaction is conducted under relatively mild conditions, i.e. under cooling or warming, and in a solvent which will not interfere with the reaction [for example, water, hydrophilic solvents such as alcohols (e.g. methanol, ethanol, propanol, etc.), acetone, N,N-dimethylformamide, tetrahydrofuran, dioxane, dimethyl sulfoxide, etc. or a mixture of such solvents].

(ii) Reduction:

Inclusive of chemical and catalytic reduction procedures, this reduction is carried out in the per se known manner.

The reducing agent employed for chemical reduction includes, among others, combinations of a metal (e.g. tin, zinc, iron, etc.) or a metal compound (e.g. chronium chloride, chromium acetate, etc.) with an organic or inorganic acid (e.g. formic acid, acetic acid, propionic acid, trifluoroacetic acid, p-toluenesulfonic acid, hydrochloric acid, hydrobromic acid, etc.).

Preferred examples of the catalyst for catalytic reduction include platinum catalysts (e.g. platinum plate, platinum sponge, platinum black, platinum colloid, platinum oxide, platinum wire, etc.), palladium catalysts (e.g. palladium sponge, palladium black, palladium oxide, palladium-on-carbon, palladium colloid, palladium-on-barium sulfate, palladium-on-barium carbonate, etc.), nickel catalysts (e.g. reducing nickel, nickel oxide, Raney nickel, etc.), cobalt catalysts (e.g. reducing cobalt, Raney cobalt, etc.), iron catalysts (e.g. reducing iron, Raney iron, etc.), copper catalysts (e.g. reducing copper, Raney copper, Ullmann copper, etc.) and so forth.

This reduction reaction is generally carried out in a solvent. Preferred examples of the solvent include water and the common organic solvents such as alcohols (e.g. methanol, ethanol, propanol, etc.), acetic acid, etc., and mixtures thereof. The liquid acids mentioned hereabove for chemical reduction may also be used as the solvent. As further preferred examples of the solvent for catalytic reduction, there may be mentioned diethyl ether, dioxane, tetrahydrofuran, etc. as well as mixtures thereof.

This reaction proceeds fast under comparatively mild conditions, e.g. under cooling or warming.

(3) Process 3-3:

Simultaneous elimination of amino-, guanidino-, carboxy- and hydroxy-protecting groups:

Depending on the species of amino-, guanidino-, carboxy- and hydroxy-protecting groups, these sets of protective groups are removed in a single operation by the above-mentioned amino- and guanidino-protecting group elimination reaction and carboxy- and hydroxy-protecting group elimination reaction, respectively. However, the most advantageous reaction for simultaneous elimination of the amino-, guanidino-, carboxy- and hydroxy-protecting groups is a treatment with an acid such as hydrogen fluoride, methanesulfonic acid, trifluoromethanesulfonic acid, etc. This reaction can be conducted using such an acid in the presence or absence of the common solvent which will not interfere with the reaction.

In many instances, satisfactory results are obtained when the reaction is conducted in the presence of anisole, dimethyl sulfide or the like.

The above-mentioned acid can also be utilized as the solvent as well.

Generally, this reaction is preferably conducted under cooling or in the neighborhood of 0° C.

The compounds (I) through (XVI) and compounds ($I^a$) through ($XVI^a$) according to this invention each includes one or more isomers due to intramolecular asymmetric carbon atoms. Such isomers are all subsumed in the scope of this invention.

The compounds (I) through (XVI) and pharmaceutically acceptable salts thereof, which are provided by this invention, have immunomodulating activities such as immunopotentiating activity and are, therefore, of value as antimicrobial agents, antivirus agents and so forth.

The following test examples are presented to illustrate the protective effects of some representative species of the novel peptide of this invention against infectious diseases caused by bacteria or virus.

(1) Test 1 (protective effect against bacterial infection)
(a) Method:
Test animals: ICR strain mice, males, 4 weeks old, 10 to 20 animals per group.
Administration schedule: The peptides of this invention in predetermined concentrations (aqueous solutions) were intraperitoneally administered 7, 6, 3, 2 and 1 day before infection.
Method of bacterial infection: *Escherichia coli* No. 22, cultured at 37° C. for 20 hours (concentration: $2.0 \times 10^8$ cfu/ml), was suspended in sterile physiological saline and the test mice were intraperitoneally inoculated with 0.5 ml of the suspension. The mice were observed for death over a period of 4 days after infection and the survival rate (%) was calculated.
(b) Results

| Peptide of this invention (Example No.) | Dosage (mg/kg) | Survival rate (%) |
| --- | --- | --- |
| Example 6-(2) | 1.0 | 60 |
|  | 0.1 | 40 |
|  | 0.01 | 70 |
|  | 0 | 10 |
| Example 7-(2) | 1.0 | 40 |
|  | 0.1 | 70 |
|  | 0.01 | 50 |
|  | 0 | 10 |

(2) Test 2 (protective effect against bacterial infection)
(a) Method:
Test animals: Same as Test 1.
Administration schedule: Each peptide of this invention in predetermined concentrations (aqueous solutions) was intraperitoneally administered 6, 5, 4 and 1 day before infection.
Method of bacterial infection: Same as Test 1.
(b) Results:

| Peptide of this invention (Example No.) | Dosage (mg/kg) | Survival rate (%) |
| --- | --- | --- |
| Example 1-(2) | 1 | 40 |
|  | 0.1 | 40 |
| Example 4-(2) | 1 | 50 |
| Example 5-(2) | 1 | 50 |
| Control | 0 | 20 |

(3) Test 3 (protective effect against bacterial infection)
(a) Method:
Test animals: Same as Test 1
Administration schedule: Each peptide of this invention in predetermined concentrations (aqueous solutions) was intraperitoneally administered 8, 7, 4, 3 and 2 days before infection.
Method of bacterial infection: Same as Test 1.
(b) Results:

| Peptide of this invention (Example No.) | Dosage (mg/kg) | Survival rate (%) |
| --- | --- | --- |
| Example 8-(2) | 1.0 | 90 |
|  | 0.1 | 60 |
|  | 0.01 | 80 |
|  | 0 | 20 |
| Example 9-(2) | 1.0 | 70 |
|  | 0.1 | 70 |
|  | 0.01 | 70 |
|  | 0 | 20 |
| Example 10-(2) | 1.0 | 70 |
|  | 0.1 | 60 |
|  | 0.01 | 50 |
|  | 0 | 20 |
| Example 11-(2) | 1.0 | 70 |
|  | 0.1 | 50 |
|  | 0.01 | 70 |
|  | 0 | 20 |
| Example 12-(2) | 1.0 | 50 |
|  | 0.1 | 50 |
|  | 0.01 | 70 |
|  | 0 | 20 |
| Example 14-(2) | 1.0 | 70 |
|  | 0.1 | 50 |
|  | 0.01 | 50 |
|  | 0 | 20 |
| Example 15-(2) | 1.0 | 80 |
|  | 0.1 | 100 |
|  | 0.01 | 80 |
|  | 0 | 20 |

(4) Test 4 (protective effect against virus infection)
(a) Method:
Test animals: Same as Test 1.
Administration schedule: Each peptide of this invention in predetermined concentrations (aqueous solutions) was intraperitoneally administered 8, 7, 4, 3 and 2 days before infection.
Method of virus infection: *Herpes simplex* virus type 1 Miyama strain (concentration: $2 \times 10^3$ pfu/ml) was suspended in sterile physiological saline and 0.2 ml of the suspension was intraperitoneally inoculated. The mice was observed for death over a period of 14 days after infection and the survival rate (%) was calculated.

| Peptide of this invention (Example No.) | Dosage (mg/kg) | Survival rate (%) |
|---|---|---|
| Example 1-(2) | 1 | 60 |
| | 0.1 | 40 |
| | 0.01 | 80 |
| | 0 | 0 |

(5) Test 5 (protective effect against bacterial infection)
(a) Method:
Test animals: ICR strain mice, males, 4 weeks old, 10 to 20 animals per group.
Administration schedule: The peptides of this invention in predetermined concentrations (aqueous solutions) were intraperitoneally administered 7, 6, 3, 2 and 1 day before infection.
Method of bacterial infection: *Escherichia coli* No. 22, cultured at 37° C. for 20 hours (concentration: $2.0 \times 10^8$ cfu/ml), was suspended in sterile physiological saline and the test mice were intraperitoneally inoculated with 0.5 ml of the suspension. The mice were observed for death over a period of 4 days after infection and the survival rate (%) was calculated.
(b) Results

| Peptide of this invention (Example No.) | Dosage (mg/kg) | Survival rate (%) |
|---|---|---|
| Example 18-(2) | 1.0 | 80 |
| | 0.1 | 70 |
| | 0.01 | 60 |
| | 0 | 10 |

(6) Test 6 (protective effect against virus infection)
(a) Method:
Test animals: Same as Test 5.
Administration schedule: Each peptide of this invention in aqueous solution was intraperitoneally administered 8, 7, 4, 3 and 2 days before infection (0.01 mg/kg).
Method of virus infection: *Herpes simplex* virus type 1 Miyama strain (concentration: $2 \times 10^3$ pfu/ml) was suspended in sterile physiological saline and 0.2 ml of the suspension was intraperitoneally inoculated. The mice was observed for death over a period of 14 days after infection and the survival rate (%) was calculated.
(b) Results:

| Peptide of this invention (Example No.) | Survival rate (%) |
|---|---|
| Example 16-(4) | 85 |
| Example 17-(2) | 90 |
| Control | 55 |

Pharmaceutical compositions according to this invention can be used in various dosage forms which may for example be solid, semi-solid or liquid preparations containing the active ingredient of this invention in admixture with an organic or inorganic vehicle or excipient suitable for external, oral or parenteral administration. The active ingredient can be formulated with a nontoxic, pharmaceutically acceptable vehicle or carrier which is commonly employed in the production of tablets, pellets, capsules, suppositories, solutions, emulsions, suspensions and so forth. Among the useful vehicles and carriers are water, glucose, lactose, gum arabic, gelatin, mannit, starch paste, magnesium trisilicate, talc, corn starch, gelatin, finely divided (colloidal) silica, potato starch, urea, and other substances suitable for the production of solid, semi-solid or liquid pharmaceutical preparations. In addition to such a vehicle or carrier, there may also be employed an adjuvant, stablizer, viscosity builder or thickener, colorant, flavor or/and so forth. A preservative or/and an antibacterial agent may also be incorporated for the purpose of upholding the activity of the pharmaceutical composition or active ingredient. The active ingredient compound is contained in such a pharmaceutical composition in a sufficient amount to ensure a desired therapeutic effect according to the therapy or/and disease condition to be cured.

For use in human beings, such a composition is desirably administered intravenously, intramuscularly or orally. While the dosage or therapeutically effective dose of the active ingredient of this invention depends on the age and condition of the patient to be treated, it is generally used at a dose level of about 0.1 to 1000 mg daily per kilogram body weight of a human being or animal, for therapeutic purposes. The average single dose may be about 5 mg, 50 mg, 100 mg, 250 mg or 500 mg.

This invention will be further described by way of the following production and working examples in which each amino acid is the L-compound.

PRODUCTION EXAMPLE 1

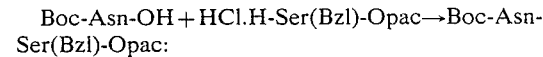

Boc-Asn-OH (510 mg), HCl.H-Ser(Bzl)-Opac (700 mg) and 1-hydroxybenzotriazole (297 mg) were dissolved in a mixture of methylene chloride (10 ml) and dimethylformamide (3 ml), and 1-ethyl-3-(3-dimethylaminopropyl)carbodiimide (341 mg) was added thereto at −50° C. The temperature was raised gradually to 0° C. over a period of 4 hours. The mixture was stirred at the same temperature for 4 hours and then poured into a mixture of ethyl acetate (50 ml) and water (50 ml). The aqueous layer was extracted with ethyl acetate. The extract was combined with the ethyl acetate layer and the mixture was washed with water, dilute hydrochloric acid, water, sodium hydrogen carbonate, water and sodium chloride in that order, dried over magnesium sulfate and concentrated. The concentrate was washed with ethyl acetate to give Boc-Asn-Ser(Bzl)-Opac (766 mg).

mp: 169–172° C. Elemental analysis (%) Calcd. for $C_{25}H_{33}N_3O_8$: C, 61.47; H, 6.30; N, 7.96 Found: C, 61.25; H, 6.28; N, 7.83 $[\alpha]_D = -5.36°$ (c=0.96, dimethylformamide)

PRODUCTION EXAMPLE 2

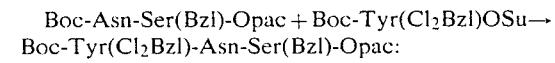

Boc-Asn-Ser(Bzl)-Opac (4.0 g) was treated with trifluoroacetic acid and, then, with dioxanehydrochloric acid to give HCl H-Asn-Ser(Bzl)-Opac. This compound was dissolved in dimethylformamide (60 ml) and the solution was neutralized with triethylamine (2.11 ml). To this solution was added Boc-Tyr(Cl₂Bzl)-Osu (4.1 g) and the mixture was stirred at room temperature for 24 hours, after which water was added at 0° C. The precipitate was collected by filtration, washed with water, and dried to give Boc-Tyr(Cl$_2$Bzl)-Asn-Ser(Bzl)-Opac (5.82 g).

mp: 204–206° C. Elemental analysis (%) Calcd. for C$_{43}$H$_{46}$N$_4$O$_{10}$Cl$_2$: C, 60.78; H, 5.46; N, 6.60 Found: C, 60.64; H, 5.74; N, 6.68 [α]$_D$= −3.38° (c=1.025, dimethylformamide)

PRODUCTION EXAMPLE 3

Boc-Tyr(Cl$_2$Bzl)-Asn-Ser(Bzl)-Opac→Boc-Tyr(Cl$_2$Bzl)-Asn-Ser(Bzl)-OH:

Zinc dust (5.0 g) was added to a mixture of Boc-Tyr(Cl$_2$Bzl)-Asn-Ser(Bzl)-Opac (5.80 g), dimethylformamide (250 ml) and acetic acid (150 ml) at room temperature. The resulting mixture was stirred at room temperature for 2 hours and 40 minutes, followed by further addition of zinc dust (1.0 g). The mixture was stirred at room temperature for 1 hour and filtered with the aid of cellulose powder. The zinc dust was washed with a mixture of methannol and acetic acid. The washings and the filtrate were combined and concentrated. To the concentrate was added water and the resulting precipitate was collected by filtration and washed with ether to give Boc-Tyr(Cl$_2$Bzl)-Asn-Ser(Bzl)-OH (4.82 g).

mp: 219–221° C. Elemental analysis (%) Calcd. for C$_{35}$H$_{40}$N$_4$O$_8$Cl$_2$.3/2H$_2$O: C, 56.60; H, 5.84; N, 7.54 Found: C, 56.77; H, 5.58; N, 7.54

PRODUCTION EXAMPLE 4

Boc-Lys(Cl-Z)-OH + H-Arg(NO$_2$)-OBzl.2TsOH→Boc-Lys(Cl-Z)-Arg(NO$_2$)-OBzl:

Boc-Lys(Cl-Z)-OH (4.15 g), H-Arg(NO$_2$)OBzl.2TsOH (6.54 g) and 1-hydroxybenzotriazole (1.35 g) were dissolved in methylene chloride (70 ml) and then triethylamine (2.02 g) was added, followed by addition of cyclohexylcarbodiimide (2.06 g) under ice-cooling. The temperature was raised to room temperature. The mixture was stirred for 4 hours and then filtered. The filtrate was concentrated and extracted with ethyl acetate. The extract was washed with water, dilute sodium hydrogen carbonate, water and sodium chloride in that order, dried over magnesium sulfate, and concentrated to give Boc-Lys(Cl-Z)-Arg(NO$_2$)-OBzl (7.29 g) as an amorphous solid.

Elemental analysis (%) Calcd. for C$_{32}$H$_{43}$N$_7$O$_9$Cl: C, 54.56; H, 6.14; N, 13.90; Cl, 5.03 Found: C, 53.56; H, 6.30; N, 13.44; Cl, 5.13 [α]$_D$= −14.62° (c=1.06, dimethylformamide)

PRODUCTION EXAMPLE 5

Boc-Lys(Cl-Z)-Arg(NO$_2$)-OBzl + Boc-Asp(OBzl)-Osu→Boc-Asp(OBzl)-Lys(Cl-Z)-Arg(NO$_2$)-OBzl:

Boc-Lys(Cl-Z)-Arg(NO$_2$)-OBzl (5.3 g) was treated with trifluoroacetic acid to give TFA H-Lys(Cl-Z)-Arg(NO$_2$)-OBzl (5.18 g). The compound was dissolved in methylene chloride (75 ml) containing triethylamine (1.02 ml), and Boc-Asp(OBzl)OSu (3.15 g) was added thereto under ice-cooling. The temperature was raised to room temperature and the mixture was stirred for 24 hours, during which time two portions of triethylamine (0.2 ml) were added thereto. To the resulting mixture was added N,N-dimethylaminopropylamine (50 μl) and the whole mixture was concentrated and extracted with ethyl acetate. The extract was washed with water, sodium hydrogen carbonate, water, dilute hydrochloric acid and sodium chloride in that order, dried over magnesium sulfate, and concentrated. The concentrate was chromatographed over a silica gel column (100 g), elution being carried out with methylene chloride-acetone (4:1), to give Boc-Asp(OBzl)-Lys(Cl-Z)-Arg(NO$_2$)-OBzl (4.97 g) as an amorphous solid.

Elemental analysis (%) Calcd. for C$_{43}$H$_{55}$N$_8$O$_{12}$Cl: C, 56.67; H, 6.08; N, 12.29; Cl, 3.89 Found: C, 56.15; H, 6.18; N, 12.15; Cl, 4.16 [α]$_D$= −18.10 (c=1.0, dimethylformamide)

PRODUCTION EXAMPLE 6

Boc-Asp(OBzl)-Lys(Cl-Z)-Arg(NO$_2$)-OBzl→Boc-Val-Asp(OBzl)-Lys(Cl-Z)-Arg(NO$_2$)-OBzl:

Boc-Asp(OBzl)-Lys(Cl-Z)-Arg(NO$_2$)-OBzl (6.72 g) was treated with trifluoroacetic acid (70 ml) to give TFA H-Asp(OBzl)-Lys(Cl-Z)-Arg(NO$_2$)-OBzl. The compound was dissolved in methylene chloride (50 ml) containing triethylamine (2.04 ml), and Boc-Val-OSu (2.33 g) was added thereto under ice-cooling. The resulting mixture was warmed to room temperature and stirred for 50 hours, followed by addition of N-methylmorpholine (1.0 ml). The resulting mixture was stirred at room temperature for 3 days, concentrated and extracted with ethyl acetate. The extract was washed with water, dilute hydrochloric acid, water and sodium chloride in that order. The precipitate was collected by filtration to give Boc-Val-Asp(OBzl)-Lys(Cl-Z)-Arg(NO$_2$)-OBzl (4.40 g). From the filtrate, there was obtained a further crop of the title compound (1.94 g).

mp: 174°–178° C. Elemental analysis (%) Calcd. for C$_{48}$H$_{64}$N$_9$O$_{13}$Cl: C, 57.05; H, 6.38; N, 12.47; Cl, 3.51 Found: C, 56.12; H, 6.25; N, 12.30; Cl, 4.02 [α]$_D$= −20.27° (c=1.03, dimethylformamide)

PRODUCTION EXAMPLE 7

Boc-Val-Asp(OBzl)-Lys(Cl-Z)-Arg(NO$_2$)-OBzl→HCl.H-Val-Asp(OBzl)-Lys(Cl-Z)-Arg(NO$_2$)-OBzl:

Boc-Val-Asp(OBzl)-Lys(Cl-Z)-Arg(NO$_2$)-OBzl (1.21 g) was treated with trifluoroacetic acid at 0° C. for 30 minutes and at room temperature for 25 minutes. The solvent was distilled off, and a 3.6N hydrochloric acid-dioxane solution was added to the residue, followed by concentration. Addition of ether to the concentrate yielded a powder of HCl.H-Val-Asp(OBzl)-Lys(Cl-Z)-Arg(NO$_2$)-OBzl (1.13 g).

mp: 80°–105° C. [α]$_D$: −14.06° (c=1.04, methanol)

PRODUCTION EXAMPLE 8

TsOH.H-Glu(OBzl)OBzl + Boc-Lys(Z)OSu→Boc-Lys(Z)-Glu(OBzl)OBzl

TsOH.H-Glu(OBzl)OBzl (2.0 g) was dissolved in a mixture of acetonitrile (50 ml) and water (10 ml). The solution was cooled to 0° C. and triethylamine (400 mg) and Boc-Lys(Z)OSu (1.91 g) were added. The mixture was stirred at 0°–5° C. for 2 hours and at room temperature for 3 hours. The solvent was distilled off and the residue was poured into a mixture of ethyl acetate (100 ml) and 2.5% hydrochloric acid. The organic layer was washed with water (50 ml×2), 2.5% sodium hydrogen carbonate (50 ml) and water (50 ml×3) in that order and dried over magnesium sulfate. The solvent was then distilled off to give Boc-Lys(Z)-Glu(OBzl)OBzl (2.70 g).

mp: 82°–84° C. Elemental analysis (%) Calcd. for C$_{38}$H$_{47}$N$_3$O$_9$: C, 66.17; H, 6.89; N, 6.09 Found: C, 66.06; H, 6.79; N, 6.21 Thin layer chromatography: Rf=0.71 [solvent: ethyl acetate-chloroform (1:1); carrier: silica gel (Merck)] [α]$_D$= −15.60° (c=0.36, dimethylformamide)

PRODUCTION EXAMPLE 9

Boc-Lys(Z)-Glu(OBzl)OBzl→Boc-Lys(Z)-Lys(Z)-Glu(OBzl)OBzl:

Boc-Lys(Z)-Glu(OBzl)OBzl (2.07 g) was treated with trifluoroacetic acid (20 ml) at room temperature for 30 minutes. The solvent was distilled off and the residue was dissolved in 50% aqueous dioxane (30 ml). The solution was cooled to 0° C. and and adjusted to pH 7–8 with triethylamine, followed by addition of a solution of Boc-Lys(Z)OSu (1.43 g) in dioxane (20 ml). The mixture was stirred at 0°–5° C. for 30 minutes and at room temperature for 15 hours, while the pH was maintained at 7–8. The reaction mixture was concentrated to 20 ml and the concentrate was poured into a mixture of ethyl acetate (80 ml) and 2% hydrochloric acid (50 ml). The organic layer was washed with water (30 ml×2), 2% sodium hydrogen carbonate (30 ml×2) and water (30 ml×3) in that order and dried over magnesium sulfate. The solvent was then distilled off. The residue was crystallized from ether to give Boc-Lys(Z)-Lys(Z)-Glu(OBzl)OBzl (2.52 g).

mp: 109°–112° C. Elemental analysis (%) Calcd. for $C_{52}H_{65}N_5O_{12}$: C, 65.60; H, 6.88; N, 7.36 Found: C, 65.16; H, 6.79; N, 7.56 Thin layer chromatography: Rf=0.34 [solvent: ethyl acetate-chloroform (1:1); carrier: silica gel (Merck)] $[\alpha]_D = -14.22°$ (c=0.244, dimethylformamide)

PRODUCTION EXAMPLE 10

Boc-Lys(Z)-Lys(Z)-Glu(OBzl)OBzl→Boc-Glu(OBzl)-Lys(Z)-Lys(Z)-Glu(OBzl)OBzl:

Boc-Lys(Z)-Lys(Z)-Glu(OBzl)OBzl (1.90 g) was treated with trifluoroacetic acid (20 ml) at 0°–5° C. for 10 minutes and at room temperature for 20 minutes. The solvent was distilled off and the residue was powderized with ether. The powder was suspended in acetonitrile (30 ml) and the suspension was neutralized with triethylamine (200 mg) with ice-cooling, followed by addition of a solution of Boc-Glu(OBzl)OSu (0.87 g) in acetonitrile (10 ml). The mixture was stirred at 0°–5° C. for an hour and at room temperature for 18 hours, while maintaining the pH at 7–8. The solvent was then distilled off and the residue was collected by filtration and washed with water (10 ml×3) and ethyl acetate (10 ml×3) in that order to give Boc-Glu(OBzl)-Lys(Z)-Lys(Z)-Glu(OBzl)OBzl (1.76 g).

mp: 145°–149° C. Elemental analysis (%) Calcd. for $C_{64}H_{78}N_6O_{15}$: C, 65.62; H, 6.71; N, 7.19 Found: C, 65.19; H, 6.71; N, 7.22 Thin layer chromatography: Rf=0.18 [solvent: ethyl acetate-chloroform (1:1); carrier: silica gel (Merck)] $[\alpha]_D = -13.46$ (c=0.277, dimethylformamide)

PRODUCTION EXAMPLE 11

TsOH.H-Glu(OBzl)OBzl→Boc-Ser(Bzl)-Glu(OBzl)OBzl:

Triethylamine (0.505 g) was added to a mixture of TsOH H-Glu(OBzl)OBzl (2.5 g), acetonitrile (60 ml) and water (20 ml) under ice-cooling. To the resulting mixture was added a solution of Boc-Ser(Bzl)OSu (1.96 g) in acetonitrile (10 ml). The whole mixture was stirred at 0°–5° C. for 30 minutes and at room temperature for 15 hours and then concentrated to 30 ml. The concentrate was poured into a mixture of ethyl acetate (80 ml) and 2% hydrochloric acid (30 ml). The organic layer was washed with water (30 ml×2), 2.5% sodium hydrogen carbonate (30 ml) and water (30 ml×3) in that order and dried over magnesium sulfate. The solvent was then distilled off to give Boc-Ser(Bzl)-Glu(OBzl)OBzl (3.3 g) as an oil.

PRODUCTION EXAMPLE 12

Boc-Ser(Bzl)-Glu(OBzl)OBzl→Boc-Lys(Z)-Ser(Bzl)-Glu(OBzl)OBzl:

Boc-Ser(Bzl)-Glu(OBzl)OBzl (3.3 g) was treated with trifluoroacetic acid (33 ml) at 0°–5° C. for 10 minutes and at room temperature for 30 minutes. After removal of the trifluoroacetic acid by distillation, the residue was dissolved in 50% dioxane (100 ml). The solution was cooled to 0° C. and adjusted to pH 7–8 with triethylamine, followed by addition of a solution of Boc-Lys(Z)OSu (2.38 g) in dioxane (30 ml). The mixture was stirred at 0°–5° C. for an hour and at room temperature for 15 hours. The solvent was distilled off and the residue was poured into ethyl acetate (150 ml). The organic layer was washed with 2.5% hydrochloric acid (50 ml), water (50 ml×2), 2.5% sodium hydrogen carbonate (50 ml) and water (50 ml×2) in that order and dried over magnesium sulfate. The solvent was then distilled off. The residue was crystallized from ether to give Boc-Lys(Z)-Ser(Bzl)-Glu(OBzl)OBzl (3.75 g).

mp: 105°–108° C. Elemental analysis (%) Calcd. for $C_{48}H_{58}N_4O_{11}$: C, 66.50; H, 6.74; N, 6.46 Found: C, 66.55; H, 6.72; N, 6.60 Thin layer chromatography: Rf=0.46 [solvent: ethyl acetate-chloroform (1:1), carrier: silica gel (Merck)] $[\alpha]_D = -11.5°$ (c=0.38, dimethylformamide)

PRODUCTION EXAMPLE 13

Boc-Lys(Z)-Ser(Bzl)-Glu(OBzl)OBzl→Boc-Leu-Lys(Z)-Ser(Bzl)-Glu(OBzl)OBzl:

Boc-Lys(Z)-Ser(Bzl)-Glu(OBzl)OBzl (2.5 g) was treated with trifluoroacetic acid (25 ml) at room temperature for 30 minutes. After removal of the solvent by distillation, the residue was powderized with ether. The powder was dissolved in 50% dioxane (100 ml) and the solution was cooled to 0° C., followed by addition of triethylamine (290 mg) and Boc-Leu-OSu (947 mg). The mixture was stirred at room temperature for 15 hours and concentrated to half its original volume. The concentrate was poured into ethyl acetate (150 ml), and the organic layer was washed with 2% hydrochloric acid (50 ml), water (50 ml×2), 2.5% sodium hydrogen carbonate (50 ml) and water (50 ml×2) in that order and dried over magnesium sulfate. The solvent was then distilled off and the residue was crystallized from ether to give Boc-Leu-Lys(Z)-Ser(Bzl)-Glu(OBzl)OBzl (2.05 g).

mp: 108°–110° C. Elemental analysis (%) Calcd. for $C_{54}H_{69}N_6O_{12}$: C, 66.17; H, 7.10; N, 7.14 Found: C, 66.09; H, 7.00; N, 7.19 Thin layer chromatography: Rf=0.43 [solvent: ethyl acetate-chloroform (1:1), carrier: silica gel (Merck)] $[\alpha]_D = -16.2°$ (c=0.60, dimethylformamide)

EXAMPLE 1

Production of H-Ser-Lys-Leu-Lys-Ser-Asn-Ser-Thr-His-Gln-OH (1) Resin→Boc-Ser(Bzl)-Lys(Cl-Z)-Leu-Lys(Cl-Z)-Ser(Bzl)-Asn-Ser(Bzl)-Thr(Bzl)-His(Tos)-Glu(-resin)OBzl (1):

Benzhydrylamine resin (styrene-2% divinylbenzene copolymer) hydrochloride (0.4 mM/g) (3.0 g) was placed in a solid-phase reaction vessel, and a series of couplings was performed with Boc-Glu(OH)-OBzl, Boc-His(Tos)-OH, Boc-Thr(Bzl)-OH, Boc-ser(Bzl)-OH, Boc-Asn-OH, Boc-Ser(Bzl)-OH, Boc-Lys(Cl-Z)-OH, Boc-Leu-OH, Boc-Lys(Cl-Z)-OH and Boc-Ser(Bzl)-OH in that order according to the schedule given below.

Schedule

| Step | Reagent or solvent | Time (min.) × Number of repetitions |
|---|---|---|
| 1 (Washing) | Methylene chloride | 3 × 3 |
| 2 (Deprotection) | 50% (v/v) trifluoroacetic acid-methylene chloride | 30 × 1 |
| 3 (Washing) | Methylene chloride | 3 × 3 |
| 4 (Washing) | 2-Propanol | 3 × 2 |
| 5 (Washing) | Methylene chloride | 3 × 2 |
| 6 (Neutralization) | 5% (v/v) triethylamine-methylene chloride | 3 × 2 |
| 7 (Washing) | Methylene chloride | 3 × 3 |
| 8 (Coupling) | A solution of amino acid (3 moles) and dicyclohexylcarbodiimide (3 moles) in methylene chloride | 3–5 hours × 1 |
| 9 (Washing) | Methylene chloride | 3 × 5 |
| 10 (Washing) | 2-Propanol | 3 × 3 |
| 11 (Washing) | Dimethylformamide | 3 × 3 |

Note
The coupling with Boc—Glu(OH)—OBzl was started from step 5. The coupling step (step 8) with Boc—Asn—OH was conducted in methylene chloride-dimethylformamide (1:1) in the presence of 1-hydroxybenzotriazole. Unless otherwise specified, the reactions in each coupling in accordance with the above schedule was conducted at room temperature.

After the last coupling was finished according to the above schedule, the reaction product was washed with methanol and dried under reduced pressure to give Boc-Ser(Bzl)-Lys(Cl-Z)-Leu-Lys(Cl-Z)-Ser(Bzl)-Asn-Ser(Bzl)-Thr(Bzl)-His(Tos)-Glu(resin)OBzl (1) (5.56 g).

(2) Compound (1)→H-Ser-Lys-Leu-Lys-Ser-Asn-Ser-Thr-His-Gln-OH (2):

Boc-Ser(Bzl)-Lys(Cl-Z)-Leu-Lys(Cl-Z)-Ser(Bzl)-Asn-Ser(Bzl)-Thr(Bzl)-His(Tos)-Glu(resin)OBzl (1) (5.25 g) was treated with hydrogen fluoride (55 ml) in the presence of anisole (5.5 ml) at 0° C. for an hour. After removal of the hydrogen fluoride by distillation, 0.5N acetic acid (100 ml) and ether (20 ml) were added to the residue. The mixture was stirred under ice-cooling for an hour and then filtered. The aqueous layer of the filtrate was passed through Dowex 1×2 (acetate form) (400 ml) and the effluent was lyophilized to give a crude powder (597.5 mg). This crude powder (597 mg) was subjected to chromatography using Whatman CM-52. (3.2×56 cm) preliminarily equilibrated with 0.1M-pyridine-acetic acid buffer (pH 5.1). The column was eluted in the manner of linear concentration gradient elution with 0.1–0.5M pyridine-acetic acid buffer (pH 5.4) (1 l each), and the main fractions were combined and lyophilized. The lyophilisate was chromatographed on a Sephadex LH-20 column (3.2×65 cm), elution being carried out with 1% acetic acid. The main fractions were combined and lyophilized to give H-Ser-Lys-Leu-Lys-Ser-Asn-Ser-Thr-His-Gln-OH (2) (280 mg).

Amino acid analysis (acid decomposition) (6N hydrochloric acid, 110° C., 24 hours): Asp: 1.00, Thr: 0.93, Ser: 2.55, Glu: 1.02, Leu: 1.09, Lys: 2.00, His: 1.03 Amino acid analysis (enzymatic decomposition): The final product (1.61 mg) and 1.0 unit of aminopeptidase M (Sigma) were incubated in 0.1M ammonium hydrogen carbonate (500 ml) at 37° C. for 24 hours, followed by amino acid analysis. Ser: 2.85, Leu:1.00, Lys: 1.78, His: 0.84 (Thr, Asn and Gln not determined.) Elemental analysis (%) Calcd. for $C_{46}H_{80}N_{16}O_{17} \cdot 6H_2O \cdot 2CH_3COOH$: C, 44.24; H, 7.42; N, 16.51 Found: C, 44.58; H, 7.30; N, 15.91 Thin layer chromatography: Rf=0.24 [solvent: n-butanol-acetic acid-water-pyridine (3:1:2:1); cellulose plate: Merck No. 5552] High performance liquid chromatography: Pump: Waters 6000A (Waters) Column: Nucleosil $5C_{18}$ (150 mm × 4 mm) Eluent: 0.1M phosphoric acid-dipotassium hydrogen phosphate buffer pH 4.5: acetonitrile (8:2) Flow rate: 1.0 ml/min. Detection: UV 210 nm Retention time: 7.8 min. $[\alpha]_D = -52.67°$ (c=1.036, water)

EXAMPLE 2

Production of H-Ser-Val-Arg-Ser-Lys-Lys-Thr-Ala-Lys-Trp-Asn-OH:

(1) Resin→Boc-Ser(Bzl)-Val-Arg(Tos)-Ser(Bzl)-Lys(Cl-Z)-Lys(Cl-Z)-Thr(Bzl)-Ala-Lys(Cl-Z)-Trp(CHO)-Asp(resin)OBzl (1):

Benzhydrylamine resin (styrene-2% divinylbenzene copolymer) (0.4 mM/g) was placed in a solid-phase reaction vessel, and a series of couplings was performed with Boc-Asp(OH)-OBzl, Boc-Trp(CHO)-OH, Boc-Lys(Cl-Z)-OH, Boc-Ala-OH, Boc-Thr(Bzl)-OH, Boc-Lys(Cl-Z)-OH, Boc-Lys(Cl-Z)-OH, Boc-Ser(Bzl)-OH, Boc-Arg(Tos)-OH, Boc-Val-OH and Boc-Ser(Bzl)-OH in that order according to the schedule described in Example 1-(1). The coupling with Boc-Asp(OH)-OBzl was started from step 5. The coupling step (step 8) with Boc-Arg(Tos)-OH was performed in methylene chloride-dimethylformamide (2:1). In the treatment in step 2 in each protected amino acid coupling procedure subsequent to the coupling with Boc-Trp(CHO)-OH, the 50% (v/v) trifluoroacetic acid-methylene chloride was supplemented with 5% (v/v) ethanedithiol.

After completion of the last coupling, the product obtained was washed with ethanol and dried under reduced pressure to give Boc-Ser(Bzl)-Val-Arg(Tos)-Ser(Bzl)-Lys(Cl-Z)-Lys(Cl-Z)-Thr(Bzl)-Ala-Lys(Cl-Z)-Trp(CHO)-Asp(resin)OBzl (1) (7.763 g).

Amino acid analysis (acid decomposition) [Propionic acid-concentrated hydrochloric acid (1:1), 110° C., 24 hours] Asp: 1.33, Thr: 0.96, Ser: 1.03, Ala: 1.24, Val: 1.00, Lys: 2.99, Arg: 1.02

(2) Compound (1)→H-Ser-Val-Arg-Ser-Lys-Lys-Thr-Ala-Lys-Trp-Asn-OH (2):

Boc-Ser(Bzl)-Val-Arg(Tos)-Ser(Bzl)-Lys(Cl-Z)-Lys(Cl-Z)-Thr(Bzl)-Ala-Lys(Cl-Z)-Trp(CHO)-Asp(resin)OBzl (1) (3.812 g), anisole (4.0 ml) and dimethyl sulfide (3.5 ml) were placed in a Teflon reactor tube attached to a hydrogen fluoride reaction apparatus (type I, distributed by Peptide Research Institute). Hydrogen fluoride (50 ml) was condensed by cooling with dry ice-acetone. The dry ice-acetone bath was replaced with an ice water-salt bath and, after stirring for an hour, the hydrogen fluoride was distilled off under reduced pressure over 3 hours while maintaining the mixture at the bath temperature for 2 hours and then at room temperature for an hour. To the residue were added 1N acetic acid (100 ml), ether (50 ml) and toluene (30 ml) and the mixture was stirred with cooling for an hour and then filtered. The aqueous layer of the filtrate was passed through a column (300 ml) of Dowex 1×2 (acetate form) and the effluent was lyophilized to give crude H-Ser-Val-Arg-Ser-Lys-Lys-Thr-Ala-Lys-Trp(CHO)-Asn-OH (2) (967 mg).

(3) Compound (2)→H-Ser-Val-Arg-Ser-Lys-Lys-Thr-Ala-Lys-Trp-Asn-OH (3):

H-Ser-Val-Arg-Ser-Lys-Lys-Thr-Ala-Lys-Trp(CHO)-Asn-OH (2) (965 mg) was dissolved in 0.1M ammonium hydrogen carbonate (90 ml) and the solution was stirred at 37°–38° C. for 24 hours, followed by addition of 0.1M ammonium hydrogen carbonate (4.5 g). The mixture was further stirred at 43° C. for 24 hours and then concentrated. The concentrate was chromatographed on a Sephadex G-25 column (3.2×65 cm), elution being carried out with 1N acetic acid, to give crude H-Ser-Val-Arg-Ser-Lys-Lys-Thr-Ala-Lys-Trp-Asn-OH (3).

This crude product was subjected to chromatography using a carboxymethylcellulose (Whatman CM-52) column (3.6×65 cm) preliminarily equilibrated with 0.15M ammonium acetate. The column was eluted in the manner of linear concentration gradient elution with 0.15–0.7M ammonium acetate (1,200 ml each) and 0.7–1.2M ammonium acetate (15 ml each). The fractions containing the desired product were combined and concentrated. The residue was subjected to chromatography on a Sephadex LH-20 column (3.6×93 cm), elution being carried out with 1% acetic acid. The eluate was lyophilized to give half-purified H-Ser-Val-Arg-Ser-Lys-Lys-Thr-Ala-Lys-Trp-Asn-OH (3) (470 mg).

This half-purified product was subjected to partition chromatography using a Sephadex G-25 column (3.2×65 cm) as the carrier and n-butanol-ethanol-2M ammonium acetate (4:2:5) as the solvent system. The fractions containing the desired product were combined, and concentrated. The residue was chromatographed on a Sephadex LH-20 column (3.6×87 cm), elution being carried out with 1% acetic acid, to give purified H-Ser-Val-Arg-Ser-Lys-Lys-Thr-Ala-Lys-Trp-Asn-OH (3) (425 mg).

Amino acid analysis (acid decomposition) (4N methanesulfonic acid containing 0.2% tryptamine, 110° C., 24 hours): Asp: 1.02, Thr: 0.91, Ser: 1.82, Ala: 1.00, Val: 0.97, Lys: 3.51, Arg: 0.92, Trp: 0.90 Amino acid analysis (enzymatic decomposition): The final compound (1.09 mg) and 0.98 unit of aminopeptidase M were incubated in 240 μl of 0.1M ammonium hydrogen carbonate at 37° C. for 24 hours, followed by amino acid analysis. Ser: 2.10, Ala: 1.00, Val: 1.05, Lys: 3.06, Arg: 0.99, Trp: 1.0 (Thr and Asn not determined) Thin layer chromatography: Rf=0.40 [solvent: n-butanol-acetic acid-water-pyridine (3:1:2:1), cellulose plate: Merck No. 5552] High performance liquid chromatography: Pump: Waters 6000A (Waters) Column: Nucleosil 10C$_{18}$ (250 mm×4 mm) Eluent: 0.1M phosphoric acid-dipotassium hydrogen phosphate buffer (pH 2.7)-acetonitrile (92:8) Flow rate: 1.5 ml/min. Detection: UV 210 nm Retention time: 5.2 min. $[α]_D = -61.58°$ (c=0.526, water)

EXAMPLE 3

Production of H-Ile-Lys-Ser-Val-Arg-Ser-Lys-Lys-Thr-Ala-Lys-Trp-Asn-OH:

(1) Boc-Ser(Bzl)-Val-Arg(Tos)-Ser(Bzl)-Lys(Cl-Z)-Lys(Cl-Z)-Thr(Bzl)-Ala-Lys(Cl-Z)-Trp(CHO)-Asp(resin)OBzl (1)→Boc-Ile-Lys(Cl-Z)-Ser(Bzl)-Val-Arg(Tos)-Ser(Bzl)-Lys(Cl-Z)-Lys(Cl-Z)-Thr(Bzl)-Ala-Lys(Cl-Z)-Trp(CHO)-Asp(resin)OBzl (2):

Boc-Ser(Bzl)-Val-Arg(Tos)-Ser(Bzl)-Lys(Cl-Z)-Lys(Cl-Z)-Thr(Bzl)-Ala-Lys(Cl-Z)-Trp(CHO)-Asp(resin)OBzl (1) [resin: benzhydrylamine resin (styrene-2% divinylbenzene copolymer)] (3.95 g) was placed in a solid-phase reaction vessel and coupled with Boc-Lys(Cl-Z)-OH and Boc-Ile-OH in that order in accordance with the schedule described in Example 1-(1). Thereafter, the reaction product was washed with methanol and dried under reduced pressure to give Boc-Ile-Lys(Cl-Z)-Ser-(Bzl)-Val-Arg(Tos)-Ser(Bzl)-Lys(Cl-Z)-Lys(Cl-Z)-Thr(Bzl)-Ala-Lys(Cl-Z)-Trp(CHO)-Asp(resin)OBzl (2) (4.193 g).

Amino acid analysis (acid decomposition) [Propionic acid-concentrated hydrochloric acid (1:1), 110° C., 24 hours]: Asp: 1.46, Thr: 0.91, Ser: 0.67, Ala: 1.24, Val: 1.00, Ile: 0.96, Lys: 1.04×4, Arg: 1.00, Trp (undeterminable due to decomposition)

(2) Compound (2)→H-Ile-Lys-Ser-Val-Arg-Ser-Lys-Lys-Thr-Ala-Lys-Trp(CHO)-Asn-OH (3):

Boc-Ile-Lys(Cl-Z)-Ser(Bzl)-Val-Arg(Tos)-Ser(Bzl)-Lys(Cl-Z)-Lys(Cl-Z)-Thr(Bzl)-Ala-Lys(Cl-Z)-Trp(CHO)-Asp(resin)OBzl (2) (3.935 g) was treated with hydrogen fluoride (40 ml) in the presence of anisole (4.0 ml) and dimethyl sulfide (3.5 ml) at 0° C. for an hour. After removal of the hydrogen fluoride by distillation, 1N acetic acid (100 ml) and ether (50 ml) were added to the residue. The mixture was stirred for 90 minutes and filtered. The filtrate was passed through Dowex 1×2 (acetate form) (300 ml) and the effluent was lyophilized to give H-Ile-Lys-Ser-Val-Arg-Ser-Lys-Lys-Thr-Ala-Lys-Trp(CHO)-Asn-OH (3) (1.134 g).

(3) Compound (3)→H-Ile-Lys-Ser-Val-Arg-Ser-Lys-Lys-Thr-Ala-Lys-Trp-Asn-OH (4):

H-Ile-Lys-Ser-Val-Arg-Ser-Lys-Lys-Thr-Ala-Lys-Trp(CHO)-Asn-OH (3) (460 mg) was treated with 0.15M ammonium hydroxide (200 mg) at room temperature for 40 minutes. The reaction mixture was neutralized with acetic acid (2.5 ml) and concentrated. The concentrate was chromatographed on a Sephadex LH-20 column (3.2×65 cm, 1% acetic acid) for desalting and lyophilized to give crude H-Ile-Lys-Ser-Val-Arg-Ser-Lys-Lys-Thr-Ala-Lys-Trp-Asn-OH (4) (443 mg).

This crude product (1.06 g) was subjected to chromatography using a carboxymethylcellulose (Whatman CM-52) column (3.2×65 cm) equilibrated with 0.1M ammonium acetate. The column was eluted in the manner of linear concentration gradient elution with 0.1–0.5M ammonium acetate (1200 ml each) and 0.5–1.0M ammonium acetate (1000 ml each). The main fractions were combined and concentrated and the concentrate was desalted by chromatography on a Sephadex G-15 column (3.2×65 cm, 1N acetic acid) and lyophilized to give half-purified H-Ile-Lys-Ser-Val-Arg-Ser-Lys-Lys-Thr-Ala-Lys-Trp-Asn-OH (4) (492 mg).

This half-purified product (443 mg) was subjected to partition chromatography using a Sephadex G-25 column (3.2×65 cm) as the carrier and n-butanol-ethanol-2M ammonium acetate (4:2:5) as the solvent system. The main fractions were combined and concentrated. The residue was desalted by chromatography on a Sephadex LH-20 column (3.2×65 cm, 1% acetic acid) and lyophilized to give purified H-Ile-Lys-Ser-Val-Arg-Ser-Lys-Lys-Thr-Ala-Lys-Trp-Asn-OH (4) (280 mg).

Amino acid analysis (acid decomposition) (4N methanesulfonic acid containing 0.2% tryptamine, 110° C., 24 hours): Asp: 1.03, Thr: 0.96, Ser: 1.74, Ala: 1.00, Val: 0.95, Ile: 1.05, Lys: 3.92, Arg: 0.94, Trp: 1.10 Amino acid analysis (enzymatic decomposition): The final product (1.18 mg) and 0.98 unit of aminopeptidase M were incubated in 240 μl of 0.1M ammonium hydrogen carbonate at 37° C. for 24 hours, followed by amino acid analysis. Ser: 1.92, Ala: 1.00, Val: 1.01, Ile: 1.09, Lys: 4.00, Arg: 1.00, Trp: 1.0 (Thr and Asn not determined) Thin layer chromatography: Rf=0.41 [solvent: n-butanol-acetic acid-water-pyridine (3:1:2:1), cellulose plate: Merck No. 5552] High performance liquid chromatography: Pump: Waters 6000A (Waters) Column: Nucleosil 10C$_{18}$ (250 mm×4 mm) Eluent: 0.1M phosphoric acid-dipotassium hydrogen phosphate buffer (pH 2.7)-acetonitrile (92:8) Flow rate: 1.5 ml/min. Detection: UV 210 nm Retention time: 6.8 minutes $[\alpha]_D = -63.0°$ (c=0.424, water)

EXAMPLE 4

Production of H-Glu-Lys-Leu-Lys-Ser-Glu-Leu-Val-Ala-Asn-OH:

(1) Resin→Boc-Glu(OBzl)-Lys(Cl-Z)-Leu-Lys(Cl-Z)-Ser(Bzl)-Glu(OBzl)-Leu-Val-Ala-Asp(resin)OBzl (1):

Benzhydrylamine resin (styrene-2% divinylbenzene copolymer) hydrochloride (0.4 mM/g) (4.0 g) was coupled with Boc-Asp(OH)-OBzl, Boc-Ala-OH, Boc-Val-OH, Boc-Leu-OH, Boc-Ser(Bzl)-OH, Boc-Glu(OBzl)-OH, Boc-Lys(Cl-Z)-OH, Boc-Leu-OH, Boc-Lys(Cl-Z)-OH and Boc-Glu(OBzl)-OH in that order in accordance with the schedule and methods described in Example 1-(1) and 2-(1). There was obtained Boc-Glu(OBzl)-Lys(Cl-Z)-Leu-Lys(Cl-Z)-Ser(Bzl)-Glu(OBzl)-Leu-Val-Ala-Asp(resin)OBzl (1) (6.903 g).

(2) Compound (1)→H-Glu-Lys-Leu-Lys-Ser-Glu-Leu-Val-Ala-Asn-OH (2):

Boc-Glu(OBzl)-Lys(Cl-Z)-Leu-Lys(Cl-Z)-Ser(Bzl)-Glu-OBzl)-Leu-Val-Ala-Asp(resin)OBzl (1) (3.298 g) was treated with hydrogen fluoride in the presence of anisole (5 ml) at 0° C. for an hour. After removal of the hydrogen fluoride by distillation, 1N acetic acid (80 ml) and ether (20 ml) were added to the residue. The mixture was stirred with cooling for an hour and filtered. The filtrate was passed through Dowex 1×2 (acetate form) (260 ml) and the effluent was lyophilized to give crude H-Glu-Lys-Leu-Lys-Ser-Glu-Leu-Val-Ala-Asn-OH (2) (800 mg).

This crude product (800 mg) was subjected to chromatography using diethylaminoethylcellulose (Whatman DE-52) column (3.2×53 cm) equilibrated with 0.1M dipotassium hydrogen phosphate-potassium dihydrogen phosphate buffer (pH 7.8). The column was washed with water and eluted in the manner of linear concentration gradient elution with 0.1–0.5M sodium chloride (1000 ml each). The main fractions were combined and passed through a Sephadex G-15 column (3.2×65 cm, 0.1% acetic acid) for desalting to give half-purified H-Glu-Lys-Leu-Lys-Ser-Glu-Leu-Val-Ala-Asn-OH (2) (626 mg).

This half-purified product (442 mg) was subjected to partition chromatography using a Sephadex G-25 column (3.2×65 cm) as the carrier and n-butanol-ethanol-2M ammonium acetate (4:2:5) as the solvent system. The main fractions were combined and passed through a Sephadex G-25 column (3.2×65 cm, 0.5N acetic acid) for desalting to give purified H-Glu-Lys-Leu-Lys-Ser-Glu-Leu-Val-Ala-Asn-OH (2) (419 mg).

Amino acid analysis (acid decomposition) (6N hydrochloric acid, 110° C., 24 hours): Asp: 1.10, Ser: 0.94, Glu: 2.20, Ala: 1.17, Val: 1.00, Leu: 2.24, Lys: 2.14 Amino acid analysis (enzymatic decomposition):

The final product (1.60 mg) and 1.0 unit of aminopeptidase M were incubated in 500 μl of 0.1M ammonium hydrogen carbonate at 37° C. for 24 hours, followed by amino acid analysis.

Ser: 1.17, Glu: 2.16, Ala: 1.11, Val: 1.00, Leu: 2.16, Lys: 2.12 (Asn not determined) Elemental analysis (%) Calcd. for C$_{49}$H$_{87}$N$_{13}$O$_{17}$.7H$_2$O.2CH$_3$COOH: C, 46.25; H, 7.98; N, 13.23 Found: C, 45.92; H, 7.05; N, 13.49 Thin layer chromatography: Rf=0.5 [solvent: n-butanol-acetic acid-water-pyridine (3:1:2:1); carrier: cellulose plate, Merck No. 5552] High performance liquid chromatography: Pump: Waters 6000A (Waters) Column: Nucleosil 5C$_{18}$ (150 mm×4) Eluent: 0.1M phosphoric acid-dipotassium hydrogen phosphate buffer (pH 4.5)-acetonitrile (90:10) Flow rate: 1.0 ml/min. Detection: UV 210 nm Retention time: 5.4 minutes $[\alpha]_D = -73.3°$ (c=0.436, water)

EXAMPLE 5

Production of H-Thr-Lys-Glu-Lys-Leu-Lys-Ser-Glu-Leu-Val-Ala-Asn-OH:

(1) Boc-Glu(OBzl)-Lys(Cl-Z)-Leu-Lys(Cl-Z)-Ser(Bzl)-Glu-(OBzl)-Leu-Val-Ala-Asp(resin)OBzl→Boc-Thr(Bzl)-Lys(Cl-Z)-Glu(OBzl)-Lys(Cl-Z)-Leu-Lys(Cl-Z)-Ser(Bzl)-Glu(OBzl)-Leu-Val-Ala-Asp(resin)OBzl (1):

Boc-Glu(OBzl)-Lys(Cl-Z)-Leu-Lys(Cl-Z)-Ser(Bzl)-Glu(OBzl)-Leu-Val-Ala-Asp(resin)OBzl (3.40 g) was coupled with Boc-Lys(Cl-Z)-OH and Boc-Thr(Bzl)-OH in that order in accordance with the schedule and method described in Example 1-(1). There was obtained Boc-Thr-(Bzl)-Lys(Cl-Z)-Glu(OBzl)-Lys(Cl-Z)-Leu-Lys(Cl-Z)-Ser(Bzl)-Glu(OBzl)-Leu-Val-Ala-Asp(resin)OBzl (1) (3.704 g).

(2) Compound (1)→H-Thr-Lys-Glu-Lys-Leu-Lys-Ser-Glu-Leu-Val-Ala-Asn-OH (2):

Boc-Thr(Bzl)-Lys(Cl-Z)-Glu(OBzl)-Lys(Cl-Z)-Leu-Lys(Cl-Z)-Ser(Bzl)-Glu(OBzl)-Leu-Val-Ala-Asp(resin)OBzl (1) (3.527 g) was treated with hydrogen fluoride (50 ml) in the presence of anisole (5 ml) at 0° C. for an hour. The hydrogen fluoride was distilled off and 1N acetic acid (70 ml) and ether (20 ml) were added to the residue. The mixture was stirred at 0° C. for an hour and filtered. The aqueous layer of the filtrate was passed through a column of Dowex 1×2 (acetate form, 280 ml) and lyophilized to give crude H-Thr-Lys-Glu-Lys-Leu-Lys-Ser-Glu-Leu-Val-Ala-Asn-OH (2) (909.6 mg).

This crude product (909 mg) was subjected to chromatography using a carboxmethylcellulose (Whatman CM-2) column (3.2×65 cm) equilibrated with 0.1M pyridine-acetic acid buffer (pH 5.4). The column was eluted in the manner of linear concentration gradient elution with 0.1–0.3M pyridine-acetic acid buffer (pH 5.4) (1000 ml each). The main fractions were combined and lyophilized to give half-purified H-Thr-Lys-Glu-Lys-Leu-Lys-Ser-Glu-Leu-Val-Ala-Asn-OH (2) (701 mg).

This half-purified product (658 mg) was subjected to partition chromatography using a Sephadex G-25 column (3.2×65 cm) as the carrier and n-butanol-ethanol-2M ammonium acetate (4:2:5) as the solvent system. The main fractions were combined and passed through a Sephadex G-15 column (2.4×45 cm, 0.2% acetic acid) for desalting and lyophilized to give purified H-Thr-Lys-Glu-Lys-Leu-Lys-Ser-Glu-Leu-Val-Ala-Asn-OH (2) (433 mg).

Amino acid analysis (acid decomposition) (6N hydrochloric acid, 110° C., 24 hours): Asp: 1.11, Thr: 1.00, Ser: 1.01, Glu: 2.16, Ala: 1.08, Val: 1.00, Leu: 2.30, Lys: 3.15 Amino acid analysis (enzymatic decomposition):

The final product (1.36 mg) and 1.0 unit of aminopeptidase M were incubated in 500 μl of 0.1M ammonia hydrogen carbonate, followed by amino acid analysis. Thr: 1.02, Ser: 1.17, Glu: 2.18; Ala: 1.13, Val: 1.00, Leu: 2.20, Lys: 3.18 (Asn not determined) Elemental analysis (%) Calcd. for $C_{59}H_{106}N_{16}O_{20}\cdot 8H_2O\cdot 2CH_3COOH$: C, 46.12; H, 7.12; N, 13.94 Found: C, 46.56; H, 8.07; N, 13.80 Thin layer chromatography: Rf=0.19 [solvent: n-butanol-methanol-aqueous ammonia (1:2:1); carrier: silica gel (Merck No. 5714)] High performance liquid chromatography: Pump: Waters 6000A (Waters) Column: Nucleosil $15C_{18}$ (150 mm×4 mm) Eluent: 0.1M phosphoric acid-dipotassium hydrogen phosphate buffer (pH 4.5)-acetonitrile (90:10) Flow rate: 1.0 ml/min. Detection: UV 210 nm Retention time: 5.9 minutes $[\alpha]_D = -78.35°$ (c=0.394, water)

EXAMPLE 6

Production of H-Asp-Leu-Lys-Glu-Lys-Lys-Glu-Val-Val-Glu-Glu-OH:

(1) Boc-Glu(OBzl)-OCH₂-resin→Boc-Asp(OBzl)-Leu-Lys(Cl-Z)-Glu(OBzl)-Lys(Cl-Z)-Lys(Cl-Z)-Glu(OBzl)-Val-Val-Glu(OBzl)-Glu(OBzl)-OCH₂-resin (1):

Boc-Glu(OBzl)-OCH₂-resin (styrene-1% divinylbenzene copolymer; Glu content: 0.76 mM/g) (3.0 g) was coupled with Boc-Glu(OBzl)-OH, Boc-Glu(OBzl)-OH, Boc-Val-OH, Boc-Val-OH, Boc-Glu(OBzl)-OH, Boc-Lys(Cl-Z)-OH, Boc-Lys(Cl-Z)-OH, Boc-Glu(OBzl)-OH, Boc-Lys(Cl-Z)-OH, Boc-Leu-OH and Boc-Asp(OBzl)-OH in that order in accordance with the schedule and method described in Example 1-(1). There was obtained Boc-Asp(OBzl)-Leu-Lys(Cl-Z)-Glu(OBzl)-Lys(Cl-Z)-Lys(Cl-Z)-Glu(OBzl)-Val-Val-Glu(OBzl)-Glu(OBzl)-OCH₂-resin (1) (6.83 g).

(2) Compound (1)→H-Asp-Leu-Lys-Glu-Lys-Lys-Glu-Val-Val-Glu-Glu-OH (2):

Boc-Asp(OBzl)-Leu-Lys(Cl-Z)-Glu(OBzl)-Lys(Cl-Z)-Lys(Cl-Z)-Glu(OBzl)-Val-Val-Glu(OBzl)-Glu(OBzl)-OCH₂-resin (1) (3.34 g) was treated with hydrogen fluoride in the presence of anisole (4.5 ml) at 0° C. for an hour. The hydrogen fluoride was distilled off, and 1N acetic acid (100 ml) and ether (30 ml) were added. The mixture was stirred with cooling for an hour and filtered. The aqueous layer of the filtrate was chromatographed on a column (5 cm×15 cm) of Dowex 1×2 (acetate form), elution being carried out with 1N acetic acid. The main fractions were combined and lyophilized to give crude H-Asp-Leu-Lys-Glu-Lys-Lys-Glu-Val-Val-Glu-Glu-OH (2) (1.33 g).

This crude product (1.23 g) was subjected to chromatography using a dimethylaminoethylcellulose (Whatman DE-52) column (3.2×65 cm) equilibrated with 0.05M ammonium hydrogen carbonate. The column was eluted in the manner of linear concentration gradient elution with 0.05–0.4M ammonium hydrogen carbonate (1500 ml each). The main fractions were combined and lyophilized to give half-purified H-Asp-Leu-Lys-Glu-Lys-Lys-Glu-Val-Val-Glu-Glu-OH (2) (754 mg).

This half-purified product (821 mg) was subjected to chromatography using a Dowex 50W×8 column (3.2×65 cm) equilibrated with 0.2M pyridine-acetic acid buffer (pH 3.1). The column was eluted in the manner of linear concentration gradient elution with 0.1M (pH 3.1)–0.5M (pH 4.7) pyridine-acetic acid buffer (1 l each), followed by further linear concentration gradient elution with 0.5M (pH 4.7)–1.0M (pH 5.4) pyridine-acetic acid buffer (1 l each). The main fractions were combined and concentrated. The residue was chromatographed on a Sephadex LH-20 column (3.2×65 cm), and the main fractions were combined and lyophilized. There was obtained purified H-Asp-Leu-Lys-GLu-Lys-Lys-Glu-Val-Val-Glu-Glu-OH (2) (532 mg).

Amino acid analysis (acid decomposition) (6N hydrochloric acid, 110° C., 24 hours): Asp: 1.00, Glu: 3.64, Val: 1.44, Leu: 1.09, Lys: 2.73 Elemental analysis (%) Calcd. for $C_{58}H_{100}N_{14}O_{22}\cdot 7H_2O\cdot 2.5CH_3COOH$: C, 46.65; H, 7.71; N, 12.09 Found: C, 46.01; H, 7.02; N, 12.56 Thin layer chromatography: Rf=0.15 [solvent: chloroform-methanol-aqueous ammonia (2:2:1); carrier: silica gel No. 5714 (Merck)] High performance liquid chromatography: Pump: Waters 6000A (Waters) Column: Nucleosil $5C_{18}$ (150 mm×4 mm) Eluent: 0.1M phosphoric acid-dipotassium hydrogen phosphate buffer (pH 2.6)-acetonitrile (93:7) Flow rate: 1.0 ml/min. Detection: UV 210 nm Retention time: 9.21 minutes $[\alpha]_D = -75.3°$ (c=0.49, water)

EXAMPLE 7

Production of H-Thr-Lys-Asp-Leu-Lys-Glu-Lys-Lys-Glu-Val-Val-Glu-Glu-OH:

(1) Boc-Asp(OBzl)-Leu-Lys(Cl-Z)-Glu(OBzl)-Lys(Cl-Z)-Lys(Cl-Z)-Glu(OBzl)-Val-Val-Glu(OBzl)-Glu(OBzl)-OCH₂-resin→Boc-Thr(Bzl)-Lys(Cl-Z)-Asp(OBzl)-Leu-Lys(Cl-Z)-Glu(OBzl)-Lys(Cl-Z)-Lys(Cl-Z)-Glu(OBzl)-Val-Val-Glu(OBzl)-Glu(OBzl)-OCH₂-resin (1):

Boc-Asp(OBzl)-Leu-Lys(Cl-Z)-Glu(OBzl)-Lys(Cl-Z)-Lys(Cl-Z)-Glu(OBzl)-Val-Val-Glu(OBzl)-Glu(OBzl)-OCH₂-resin (3.57 g) was coupled with Boc-Lys(Cl-Z)-OH and Boc-Thr(Bzl)-OH in that order in accordance with the schedule and method described in Example 1-(1). There was obtained Boc-Thr(Bzl)-Lys(Cl-Z)-Asp(OBzl)-Leu-Lys(Cl-Z)-Glu(OBzl)-Lys(Cl-Z)-Lys(Cl-Z)-Glu(OBzl)-Val-Val-Glu(OBzl)-Glu(OBzl)-OCH₂-resin (1) (3.79 g).

(2) Compound (1)→H-Thr-Lys-Asp-Leu-Lys-Glu-Lys-Lys-Glu-Val-Val-Glu-Glu-OH (2):

Boc-Thr(Bzl)-Lys(Cl-Z)-Asp(OBzl)-Leu-Lys(Cl-Z)-Glu(OBzl)-Lys(Cl-Z)-Lys(Cl-Z)-Glu(OBzl)-Val-Val-Glu(OBzl)-Glu(OBzl)-OCH₂-resin (1) (3.68 g) was treated with hydrogen fluoride (50 ml) in the presence of anisole at 0° C. for an hour. The hydrogen fluoride was distilled off, and 1N acetic acid (100 ml) and ether (30 ml) were added to the residue. The mixture was stirred with cooling for an hour and filtered. The aqueous layer of the filtrate was chromatographed on a column (5 cm×13 cm) of Dowex 1×2 (acetate form) (250 ml). The ninhydrin-positive fractions were combined and lyophilized to give crude H-Thr-Lys-Asp-Leu-Lys-Glu-Lys-Lys-Glu-Val-Val-Glu-Glu-OH (2) (1.60 g).

This crude product (1.60 g) was subjected to chromatography using a dimethylaminoethylcellulose (Whatman DE-52) column (3.2×65 cm) equilibrated with 0.05M ammonium hydrogen carbonate. The column was eluted in the manner of linear concentration gradient elution with 0.05M–0.3M ammonium hydrogen carbonate (1.2 l each). The main fractions were combined and lyophilized to give half-purified H-Thr-Lys-Asp-Leu-Lys-Glu-Lys-Lys-Glu-Val-Val-Glu-Glu-OH (2) (538 mg).

This half-purified product (541 mg) was chromatographed on a Dowex 50W×8 column (3.2×56 cm)

equilibrated with 0.3M pyridine-acetic acid buffer (pH 3.9). The column was eluted in the manner of linear concentration gradient elution with 0.3M (pH 3.9)-0.7M (pH 4.6) pyridine-acetic acid buffer (1 l each), followed by further linear concentration gradient elution with 0.7M (pH 4.6)-1.0M (pH 5.4) pyridine-acetic acid buffer (1 l each). The main fractions were combined and concentrated. The residue was chromatographed on a Sephadex LH-20 column (3.2×65 cm), elution being carried out with 0.2% acetic acid. The main fractions were combined and lyophilized to give purified H-Thr-Lys-Asp-Leu-Lys-Glu-Lys-Lys-Glu-Val-Val-Glu-Glu-OH (2) (445 mg).

Amino acid analysis (acid decomposition) (6N hydrochloric acid, 110° C., 24 hours); Asp: 1.00, Thr: 0.97, Glu: 3.76, Val: 1.42, Leu: 1.22, Lys: 3.72 Amino acid analysis (enzymatic decomposition) The final product (1.16 mg) and 0.65 unit of aminopeptidase M were incubated in 250 μl of 0.1M ammonium hydrogen carbonate at 37° C. for 24 hours, followed by amino acid analysis. Asp: 1.00, Thr: 1.17, Glu: 4.04, Val: 2.12, Leu: 0.93, Lys: 4.00 Elemental analysis (%) Calcd. for $C_{68}H_{119}N_{17}O_{25}\cdot 8H_2O\cdot 2CH_3COOH$: C, 46.99; H, 7.83; N, 13.00 Found: C, 46.47; H, 7.19; N, 13.07 Thin layer chromatography: Rf=0.20 [solvent: n-butanol-methanol-aqueous ammonia (1:2:1), carrier: silica gel No. 5714 (Merck)] High performance liquid chromatography: Pump: Waters 6000A (Waters) Column: Nucleosil 5C$_{18}$ (150 mm×4 mm) Eluent: 0.1M phosphoric acid-dipotassium hydrogen phosphate buffer (pH 2.6)-acetonitrile (92:8) Flow rate: 1.0 ml/min. Detection: UV 210 nm Retention time: 5.8 minutes $[\alpha]_D = -78.62°$ (c=0.43, water)

EXAMPLE 8

Production of H-Asn-Val-Lys-Ala-Lys-Ile-Gln-Asp-Lys-Glu-Gly-OH:

(1) Boc-Gly-OCH$_2$-resin→Boc-Asn-Val-Lys(Cl-Z)-Ala-Lys(Cl-Z)-Ile-Gln-Asp(OBzl)-Lys(Cl-Z)-Glu(OBzl)-Gly-OCH$_2$-resin (1):

Boc-Gly-OCH$_2$-resin (chloromethylated styrene-1% divinylbenzene copolymer, Gly content: 0.706 mM/g) (4.0 g) was coupled with Boc-Glu-(OBzl)-OH, Boc-Lys(Cl-Z)-OH, Boc-Asp(OBzl)-OH, Boc-Gln-OH, Boc-Ile-OH, Boc-Lys(Cl-Z)-OH, Boc-Ala-OH, Boc-Lys(Cl-Z)-OH, Boc-Val-OH and Boc-Asn-OH in that order in accordance with the schedule and method described in Example 1-(1). There was obtained Boc-Asn-Val-Lys(Cl-Z)-Ala-Lys(Cl-Z)-Ile-Gln-Asp(OBzl)-Lys(Cl-Z)-Glu(OBzl)-Gly-OCH$_2$-resin (1) (7.85 g) [The coupling step (step 8) with Boc-Gln-OH was performed in methylene chloride-dimethylformamide (1:1) in the presence of 1-hydroxybenzotriazole].

(2) Compound (1)→H-Asn-Val-Lys-Ala-Lys-Ile-Gln-Asp-Lys-Glu-Gly-OH (2):

Boc-Asn-Val-Lys(Cl-Z)-Ala-Lys(Cl-Z)-Ile-Gln-Asp(OBzl)-Lys(Cl-Z)-Glu(OBzl)-Gly-OCH$_2$-resin (1) (3.93 g) was treated with hydrogen fluoride in the presence of anisole (5 ml) at 0° C. for an hour. The hydrogen fluoride was distilled off and water (100 ml) was added to the residue for extraction. The extract was washed with ether and chromatographed on a Dowex 1×2 column (acetate form, 200 ml), elution being carried out with water. The main fractions were combined and lyophilized to give crude H-Asn-Val-Lys-Ala-Lys-Ile-Gln-Asp-Lys-Glu-Gly-OH (2) (1.21 g).

This crude product (1.21 g) was subjected to chromatography using a carboxymethylcellulose (Whatman CM-52) column (3.2×65 cm) preliminarily equilibrated with 0.1M pyridine-acetic acid buffer (pH 5.4). The column was eluted in the manner of linear concentration gradient elution with 0.1M-0.4M pyridine-acetic acid buffer (12.5 g each). The main fractions were combined and lyophilized to give half-purified H-Asn-Val-Lys-Ala-Lys-Ile-Gln-Asp-Lys-Glu-Gly-OH (2) (812 mg). This half-purified product (762 mg) was subjected to chromatography using a carboxymethylcellulose (Whatman CM-52) column (2.6 cm×56 cm) preliminarily equilibrated with 0.2M pyridine-acetic acid buffer (pH 5.4). The column was washed with the same buffer (300 ml), followed by elution with 0.2M-0.3M pyridine-acetic acid buffer (pH 5.4) (1 l each). The main fractions were combined and lyophilized.

This lyophilisate was chromatographed on a Sephadex G-15 column (3.2×65 cm), elution being carried out with 1% acetic acid. The main fractions were combined and lyophilized to give purified H-Asn-Val-Lys-Ala-Lys-Ile-Gln-Asp-Lys-Glu-Gly-OH (2) (330 mg).

Amino acid analysis (acid decomposition) (6N hydrochloric acid, 110° C., 24 hours): Asp: 2.15, Val: 1.00, Lys: 2.90, Ala: 1.00, Ile: 0.96, Glu: 2.06, Gly: 1.00 Amino acid analysis (enzymatic decomposition): The final product (1.77 mg) and 1.0 unit of aminopeptidase M were incubated in 500 μl of 0.1M ammonium hydrogen carbonate at 37° C. for 21 hours, followed by amino acid analysis. Asp: 1.00, Glu: 1.07, Gly: 1.00, Ala: 1.03, Val: 0.50, Ile: 0.99, Lys: 2.71 (Asn and Gln not determined) Elemental analysis (%) Calcd. for $C_{52}H_{92}N_{16}O_{18}\cdot 8H_2O\cdot 3/2CH_3COOH$: C, 45.14; H, 7.85; N, 15.31 Found: C, 45.17; H, 7.01; N, 15.32 Thin layer chromatography: Rf=0.27 [solvent: n-butanol-acetic acid-water-pyridine (3:1:2:1); carrier: cellulose (Merck No. 5552)] High performance liquid chromatography: Pump: Waters 6000A (Waters) Column: Nucleosil 5C$_{18}$ (150 mm×4 mm) Eluent: 0.1M phosphoric acid-dipotassium hydrogen phosphate buffer (pH 4.5)-acetonitrile (95:5) Flow rate: 1.0 ml/min. Detection: UV 210 nm Retention time: 9.04 minutes $[\alpha]_D = -23.61°$ (c=0.506, water)

EXAMPLE 9

Production H-Lys-Ser-Lys-Leu-Lys-Lys-Thr-Glu-Thr-Gln-Glu-OH:

(1) Boc-Glu(OBzl)-OCH$_2$-resin→Boc-Lys(Cl-Z)-Ser(Bzl)-Lys(Cl-Z)-Leu-Lys(Cl-Z)-Lys(Cl-Z)-Thr(Bzl)-Glu(OBzl)-Thr(Bzl)-Gln-Glu(OBzl)-OCH$_2$-resin (1):

Boc-Glu(OBzl)-OCH$_2$-resin (styrene-1% divinylbenzene copolymer, Glu content: 0.639 mM/g) (3.0 g) was coupled with Boc-Gln-OH, Boc-Thr(Bzl)-OH, Boc-Glu(OBzl)-OH, Boc-Thr(Bzl)-OH, Boc-Lys(Cl-Z)-OH, Boc-Lys(Cl-Z)-OH, Boc-Leu-OH, Boc-Lys(Cl-Z)-OH, Boc-Ser(Bzl)-OH and Boc-Lys(Cl-Z)-OH in that order in accordance with the schedule and methods described in Example 1-(1) and Example 8-(1). There was obtained Boc-Lys(Cl-Z)-Ser(Bzl)-Lys(Cl-Z)-Leu-Lys(Cl-Z)-Lys(Cl-Z)-Thr(Bzl)-Glu(OBzl)-Thr(Bzl)-Gln-Glu(OBzl)-OCH$_2$-resin (1) (6.13 g).

(2) Compound (1)→H-Lys-Ser-Lys-Leu-Lys-Lys-Thr-Glu-Thr-Gln-Glu-OH (2):

Boc-Lys(Cl-Z)-Ser(Bzl)-Lys(Cl-Z)-Leu-Lys(Cl-Z)-Lys(Cl-Z)-Thr(Bzl)-Glu(OBzl)-Thr(Bzl)-Gln-Glu(OBzl)-OCH$_2$-resin (1) (3.0 g) was treated with hydrogen fluoride (40 ml) in the presence of anisole (4 ml) at 0° C. for an hour. The hydrogen fluoride was distilled off and water (40 ml) was added to the residue for extraction. The extract was washed with ether (20 ml) and chromatographed on a column of Dowex 1×2 (200 ml), elution being carried out with water. The ninhydrinpositive fractions were combined and lyophilized to give a crude powder (1.01 g). This crude powder (1.01 g) was chromatographed on a CM-52 column (3.3×63 cm). The column was eluted in the manner of linear concentration gradient elution with 0.4M-0.8M pyridine-acetic acid buffer (pH 5.4) (1 l each). The main fractions were combined, concentrated and lyophilized to give a powder (750 mg). This powder (600 mg) was chromatographed on a Dowex 50 column (3×45 cm). The column was eluted in the manner of linear concentration gradient elution with 0–1M sodium chloride (1 l each) in 0.1M Tris buffer (pH 8). The main fractions were combined and concentrated. The residue was chromatographed on a Sephadex G-15 column (3.3×62 cm), elution being carried out with 0.5N acetic acid. The ninhydrinpositive fractions were combined and concentrated. The concentrate was subjected to chromatography on a LH-20 column (3.3×52 cm), elution being carried out with 0.5N acetic acid, to give H-Lys-Ser-Lys-Leu-Lys-Lys-Thr-Glu-Thr-Gln-Glu-OH (2) (420 mg).

Amino acid analysis (acid decomposition) (6N hydrochloric acid, 110° C., 24 hours): Leu: 1.0, Ser: 0.85 (1); Thr: 1.86 (2), Glu: 2.73 (3), Lys: 3.52 (4) Amino acid analysis (enzymatic decomposition): The analysis was performed in substantially the same manner as in Example 8. Leu: 1.0, Ser: 1.04 (1), Thr: 2.23 (3), Glu: 1.84 (2), Lys: 3.64 (4) Thin layer chromatography: Rf=0.38 [solvent: n-butanol-acetic acid-water-pyridine (2:2:2:1), carrier: silica gel (Merck)] $[\alpha]_D = -54.66$ (c=0.269, water)

EXAMPLE 10

Production of H-Lys-Phe-Asp-Lys-Ser-Lys-Leu-Lys-Lys-Thr-Glu-Thr-Gln-Glu-OH:

(1) Boc-Lys(Cl-Z)-Ser(Bzl)-Lys(Cl-Z)-Leu-Lys(Cl-Z)-Lys(Cl-Z)-Thr(Bzl)-Glu(OBzl)-Thr(Bzl)-Gln-Glu(OBzl)-OCH₂-resin→Boc-Lys(Cl-Z)-Phe-Asp(OBzl)-Lys(Cl-Z)-Ser(Bzl)-Lys(Cl-Z)-Leu-Lys(Cl-Z)-Lys(Cl-Z)-Thr(Bzl)-Glu(OBzl)-Thr(Bzl)-Gln-Glu(OBzl)-OCH₂-resin (1):

Boc-Lys(Cl-Z)-Ser(Bzl)-Lys(Cl-Z)-Leu-Lys(Cl-Z)-Lys(CL-Z)-Thr(Bzl)-Glu(OBzl)-Thr(Bzl)-Gln-Glu(OBzl)-OCH₂-resin (styrene-1% divinylbenzene copolymer) (3.0 g) was coupled with Boc-Asp(OBzl)-OH, Boc-Phe-OH and Boc-Lys(Cl-Z)-OH in that order in accordance with the schedule and method described in Example 1-(1). There was obtained Boc-Lys(CL-Z)-Phe-Asp(OBzl)-Lys(CL-Z)-Ser(Bzl)-Lys(Cl-Z)-Leu-Lys(Cl-Z)-Lys(Cl-Z)-Thr(Bzl)-Glu(OBzl)-Thr(Bzl)-Gln-Glu(OBzl)-OCH₂-resin (1) (3.20 g).

(2) Compound (1)→H-Lys-Phe-Asp-Lys-Ser-Lys-Leu-Lys-Lys-Thr-Glu-Thr-Gln-Glu-OH (2):

Boc-Lys(Cl-Z)-Phe-Asp(OBzl)-Lys(Cl-Z)-Ser(Bzl)-Lys(Cl-Z)-Leu-Lys(Cl-Z)-Lys(Cl-Z)-Thr(Bzl)-Glu(OBzl)-Thr(Bzl)-Gln-Glu(OBzl)-OCH₂-resin (1) (3.20 g) was treated with hydrogen fluoride (50 ml) in the presence of anisole (4 ml) at 0° C. for an hour. The hydrogen fluoride was distilled off, and water (50 ml) was added for extraction. The extract was washed with ether (40 ml) and chromatographed on a column of Dowex 1×2 (200 ml), elution being carried out with water. The ninhydrin-positive eluate fractions were combined, concentrated and lyophilized to give a crude powder (1.08 g). This crude powder was chromatographed on a CM-52 column (3.6×60 cm). The column was eluted in the manner of linear concentration gradient elution with 0.4M-0.8M pyridine-acetic acid buffer (pH 5.4) (1 l each). The main fractions were combined, concentrated and lyophilized to give a powder (820 mg). This powder was chromatographed on a Biogel P-4 column (3×118 cm), elution being carried out with 1N acetic acid, to give H-Lys-Phe-Asp-Lys-Ser-Lys-Leu-Lys-Lys-Thr-Glu-Thr-Gln-Glu-OH (2) (620 mg).

Amino acid analysis (acid decomposition): (6N hydrochloric acid, 110° C., 24 hours); Phe: 1.0 (1), Leu: 1.03 (1), Ser 0.82 (1), Asp: 1.02 (1), Thr: 1.84 (2), Glu: 3.06 (3), Lys: 4.91 (5) Amino acid analysis (enzymatic decomposition): The analysis was performed in substantially the same manner as in Example 8. Phe: 1.0, Leu: 1.03 (1), Ser: 1.12 (1), Asp: 1.01 (1), Thr+Gln: 2.16 (3), Glu: 1.99 (2), Lys: 4.88 (5) Elemental analysis (%) Calcd. for $C_{75}H_{128}N_{20}O_{25} \cdot 2CH_3COOH \cdot 16H_2O$: C, 45.00; H, 7.55; N, 13.28 Found: C, 44.85; H, 6.67; N, 12.89 Thin layer chromatography: Rf=0.15 [solvent: n-butanol-acetic acid-water-pyridine (2:2:2:1)] $[\alpha]_D = -49.2$ (c=20.29, water)

EXAMPLE 11

Production of H-Glu-Gln-Glu-Lys-Gln-OH:

(1) Resin→Boc-Glu(OBzl)-Gln-Glu(OBzl)-Lys(Cl-Z)-Glu(resin)-OBzl (1):

Benzhydrylamine resin (styrene-2% divinylbenzene copolymer) hydrochloride (0.4 mM/g) (6.0 g) was coupled with Boc-Glu(OH)-OBzl, Boc-Lys(CL-Z)-OH, Boc-Glu(OBzl)-OH, Boc-Gln-OH and Boc-Glu(OBzl)-OH in that order in accordance with the schedule and methods described in Example 1-(1) and Example 8-(1). There was obtained Boc-Glu(OBzl)-Gln-Glu(OBzl)-Lys(Cl-Z)-Glu(resin)-OBzl (1) (8.65 g).

(2) Compound (1)→H-Glu-Gln-Glu-Lys-Gln-OH:

Boc-Glu(OBzl)-Gln-Glu(OBzl)-Lys(Cl-Z)-Glu(resin)OBzl (1) (4.32 g) was treated with hydrogen fluoride (50 ml) in the presence of anisole (4 ml) at 0° C. for an hour. The hydrogen fluoride was distilled off and 1N acetic acid (30 ml) was added for extraction. The extract was washed with ether (20 ml) and chromatographed on a column of Dowex 1×2 (100 ml), elution being carried out with 3N acetic acid (250 ml). The eluate was concentrated and lyophilized to give a crude powder (500 mg). This crude powder was chromatographed on a DE-52 column (3×45 cm). The column was eluted in the manner of linear concentration gradient elution with 0–0.5M sodium chloride (800 ml each) in 0.05M Tris buffer. The main fractions were combined and concentrated. The concentrate was subjected to chromatography using a Sephadex G-15 column (3.3×50 cm), elution being carried out with 0.1% acetic acid, to give H-Glu-Gln-Glu-Lys-Gln-OH (2) (250 mg).

Amino acid analysis (acid decomposition) (6N hydrochloric acid, 110° C., 24 hours): Lys: 1.0, Glu: 4.05 (4) Amino acid analysis (enzymatic decomposition) The analysis was performed in substantially the same manner as in Example 8. Lys: 1.0, Glu: 2.06 (2), Gln: 1.44 (2) Elemental analysis (%) Calcd. for $C_{26}H_{44}N_8O_{12} \cdot 3.5H_2O$: C, 43.15; H, 7.10; N, 15.48 Found: C, 43.18; H, 6.42; N, 15.48 Thin layer chromatography: Rf=0.21 [solvent: n-butanol-acetic acid-water-pyridine (3:1:2:1), carrier: cellulose] $[\alpha]_D = -39.2$ (c=0.26, water)

EXAMPLE 12

Production of H-Lys-Glu-Thr-Ile-Glu-Gln-Glu-Lys-Gln-OH:

(1) Boc-Glu(OBzl)-Gln-Glu(OBzl)-Lys(Cl-Z)-Glu(-resin)-OBzl→Boc-Lys(Cl-Z)-Glu(OBzl)-Thr(Bzl)-Ile-Glu(OBzl)-Gln-Glu(OBzl)-Lys(Cl-Z)-Glu(-resin)-OBzl (1):

Boc-Glu(OBzl)-Gln-Glu(OBzl)-Lys(Cl-Z)-Glu(-resin)-OBzl [benzhydrylamine resin (styrene-2% divinylbenzene copolymer)] (3.0 g) was coupled with Boc-Ile-OH, Boc-Thr(Bzl)-OH, Boc-Glu(OBzl)-OH and Boc-Lys(CL-Z)-OH in that order in accordance with the schedule and method described in Example 1-(1). There was obtained Boc-Lys(Cl-Z)-Glu(OBzl)-Thr(Bzl)-Ile-Glu(OBzl)-Gln-Glu(OBzl)-Lys(Cl-Z)-Glu(resin)-OBzl (1) (4.8 g).

(2) Compound (1)→H-Lys-Glu-Thr-Ile-Glu-Gln-Glu-Lys-Gln-OH (2):

Boc-Lys(Cl-Z)-Glu(OBzl)-Thr(Bzl)-Ile-Glu(OBzl)-Gln-Glu(OBzl)-Lys(Cl-Z)-Glu(resin)-OBzl (1) (4.8 g) was treated with hydrogen fluoride (60 ml) in the presence of anisole (4 ml) at 0° C. for an hour. The hydrogen fluoride was distilled off and 1N acetic acid (50 ml) was added for extraction. The extract was washed with ether (30 ml) and chromatographed on a Dowex 1×2 column (100 ml), elution being carried out with 3N acetic acid (250 ml). The eluate was concentrated and lyophilized to give a crude powder (820 mg). This powder was chromatographed on a De-52 column (3.3×45 cm). The column was eluted in the manner of linear concentration gradient elution with 0.1M-0.4M ammonium hydrogen carbonate (800 ml each). The main fractions were combined and lyophilized to give a powder (580 mg). This powder was chromatographed on a Sephadex G-15 column (3.3×62 cm), elution being carried out with 0.1% acetic acid, to give H-Lys-Glu-Thr-Ile-Glu-Gln-Glu-Lys-Gln-OH (2) (502 mg).

Amino acid analysis (acid decomposition) (6N hydrochloric acid, 110° C., 24 hours): Ile: 1.0, Glu: 5.17 (5), Lys: 1.97 (2), Thr: 0.94 (1) Amino acid analysis (enzymatic decomposition): The analysis was performed in substantially the same manner as in Example 8. Ile: 1.0, Thr+Gln: 2.11 (3), Glu: 3.04 (3), Lys: 1.95 (2) Elemental analysis (%) Calcd for $C_{47}H_{81}N_{13}O_{19}.7H_2O$: C, 44.86; H, 7.60; N, 14.47 Found: C, 44.88; H, 6.86; N, 14.39 Thin layer chromatography: Rf=0.58 [solvent: n-butanol-acetic acid-water-pyridine (2:2:2:1); carrier: cellulose (Merck)] $[\alpha]_D = -71.9$ (c=0.205, water)

EXAMPLE 13

Production of H-Tyr-Asn-Ser-Val-Asp-Lys-Arg-OH:

(1) Boc-Tyr(Cl$_2$Bzl)-Asn-Ser(Bzl)-OH+HCl.H-Val-Asp(OBzl)-Lys(Cl-Z)-Arg(NO$_2$)-OBzl→Boc-Tyr(Cl$_2$Bzl)-Asn-Ser(Bzl)-Val-Asp(OBzl)-Lys(Cl-Z)-Arg(NO$_2$)-OBzl (1):

1-Ethyl-3-(3-dimethylaminopropyl)carbodiimide (171 mg) was added dropwise to a solution of Boc-Tyr(Cl$_2$Bzl)-Asn-Ser(Bzl)-OH (0.787 g), HCl.H-Val-Asp(OBzl)-Lys(Cl-Z)-Arg(NO$_2$)-OBzl (0.947 g) and 1-hydroxybenzotriazole (0.149 g) in dimethylformamide (25 ml) at −40° C. The temperature was raised gradually to 0° C. over a period of 80 minutes. The reaction mixture was stirred for 0° C. for 2 hours and at room temperature for 16 hours and, then, concentrated. To the concentrate was added water (100 ml). The precipitate was washed with diluted hydrochloric acid, water, dilute sodium hydrogen carbonate and water in that order to give Boc-Tyr(Cl$_2$Bzl)-Asn-Ser(Bzl)-Val-Asp(OBzl)-Lys(Cl-Z)-Arg(NO$_2$)-OBzl (1) (1.66 g).

mp: 177°-190° C. (decompn.) $[\alpha]_D = -15.26°$ (c=0.852, dimethylformamide)

(2) Compound (1)→H-Tyr-Asn-Ser-Val-Asp-Lys-Arg-OH (2):

Boc-Tyr(Cl$_2$Bzl)-Asn-Ser(Bzl)-Val-Asp(OBzl)-Lys(Cl-Z)-Arg(NO$_2$)-OBzl (1) (1.45 g) was treated with hydrogen fluoride (13 ml) in the presence of anisole (2.0 ml) at 0° C. for an hour. The hydrogen fluoride was distilled off and 1N acetic acid (20 ml) was added for extraction. The extract was washed with ether and chromatographed on a Dowex 1×2 column (5.0×13 cm) (acetate form, 250 ml), elution being carried out with 1N acetic acid. The main fractions were combined and lyophilized to give a crude powder (831 mg). This crude powder (831 mg) was subjected to chromatography using a carboxymethylcellulose (Whatman CE-52) column (3.2×45 cm) preliminarily equilibrated with 0.1M pyridine-acetic acid buffer (pH 5.4). The column was eluted in the manner of linear concentration gradient elution with 0.1M-0.4M pyridine-acetic acid buffer (pH 5.4) (1 l each). The main fractions were combined and lyophilized to give a half-purified powder (631 mg). This half-purified powder (594 mg) was subjected to partition chromatography using a Sephadex G-25 column (3.2×65 cm) as the carrier and n-butanol-ethanol-2M ammonium acetate (4:2:5) as the solvent system. The main fractions were combined and chromatographed on a Sephadex G-15 column (3.2×114 cm), elution being carried out with 1N acetic acid, to give H-Tyr-Asn-Ser-Val-Asp-Lys-Arg-OH (2) (387 mg).

Amino acid analysis (acid decomposition) (6N hydrochloric acid, 110° C., 24 hours): Asp: 2.18, Ser: 0.91, Val: 1.07, Tyr: 1.00, Lys: 0.99, Arg: 0.97 Amino acid analysis (enzymatic decomposition): The final product (1.75 mg) and 0.98 unit of aminopeptidase M were incubated in 250 μl of 0.1M ammonium hydrogen carbonate at 37° C. for 24 hours, followed by amino acid analysis. Asp: 1.00, Ser: 1.01, Val: 1.00, Tyr: 1.01, Lys: 1.03, Arg: 1.02 (Asn not determined) Elemental analysis (%) Calcd. for $C_{37}H_{60}N_{12}O_{13}.4H_2O.CH_3COOH$: C, 46.24; H, 7.16; N, 16.59 Found: C, 45.84; H, 6.57; N, 16.46 Thin layer chromatography: Rf=0.37 [solvent: n-butanol-acetic acid-water-pyridine (3:1:2:1); carrier: cellulose (Merck No. 5552)] High performance liquid chromatography: Pump: Waters 6000A (Waters) Column: Nucleosil 10C$_{18}$ (150×4 mm) Eluent: 0.1M phosphoric acid-potassium phosphate buffer (pH 2.7)-acetonitrile (96:4) Flow rate: 1.5 ml/min. Detection: UV 210 nm Retention time: 8.0 minutes $[\alpha]_D = -39.96°$ (c=0.501, water)

EXAMPLE 14

Production of H-Lys-Glu-Lys-Lys-Glu-OH:

(1) Boc-Glu(OBzl)-Lys(Z)-Lys(Z)-Glu(OBzl)OBzl→Z-Lys(Z)-Glu(OBzl)-Lys(Z)-Lys(Z)-Glu(OBzl)OBzl (1):

Boc-Glu(OBzl)-Lys(Z)-Lys(Z)-Glu(OBzl)OBzl (1.17 g) was treated with trifluoroacetic acid (15 ml) in the presence of anisole (1.2 ml) at 0°-5° C. for 10 minutes and at room temperature for 30 minutes. After removal of the trifluoroactic acid by distillation, the residue was washed with water (20 ml×2) and dissolved in a mixture of acetonitrile (30 ml) and chloroform (30 ml). The solution was cooled to 0° C., and trimethylamine (101 mg) and Z-Lys(Z)OSu (511 mg) were added. The mixture was stirred at 0°-5° C. for 5 hours and at room temperature for 15 hours and then concentrated to 20 ml. The concentrate was washed with acetonitrile (10 ml) and water (10 ml×2) in that order to give Z-Lys(Z)-Glu(OBzl)-Lys(Z)-Lys(Z)-Glu(OBzl)OBzl (1) (1.27 g).

mp: 164°-168° C. $[\alpha]_D = -12.8°$ (c=0.21, dimethylformamide) Elemental analysis (%) Calcd. for $C_{81}H_{94}N_8O_{18}$: C, 66.29; H, 6.46; N, 7.64 Found: C, 66.14; H, 6.35; N, 7.76 Thin layer chromatography: Rf=0.09 [solvent: acetic acid-chloroform (1:1), carrier: silica gel (Merck)]

(2) Compound (1)→H-Lys-Glu-Lys-Lys-Glu-OH (2):

Z-Lys(Z)-Glu(OBzl)-Lys(Z)-Lys(Z)-Glu(OBzl)OBzl (1) (100 mg) was treated with hydrogen fluoride (15 ml) in the presence of anisole (0.5 ml) at 0° C. for an hour. After removal of the hydrogen fluoride by distillation, the residue was dissolved in water (20 ml). The solution was washed with ether (10 ml) and chromatographed on a Dowex 1×2 column (2.5×10 cm) (acetate form), elution being carried out with water. The ninhydrin-positive eluate fractions were combined and lyophilized to give a powder (42 mg). This powder was dissolved in 0.05M pyridine-acetic acid buffer (pH 5.4) (5 ml) and the solution was subjected to chromatography using a Whatman CM-52 column (2.5×20 cm) preliminarily equilibrated with 0.05M pyridine-acetic acid buffer (pH 5.4). The column was eluted in the manner of linear concentration gradient elution with 0.05M-0.4M pyridine-acetic acid buffer (pH 5.4) (200 ml each). The main fractions were combined, concentrated and lyophilized to give a powder (35 mg). This powder was dissolved in 0.1% acetic acid (3 ml) and the solution was chromatographed on a Sephadex G-25 column (2.5×23 cm), elution being carried out with 0.1% acetic acid. The main fractions were combined and lyophilized to give H-Lys-Glu-Lys-Lys-Glu-OH (2) (26 mg).

Amino acid analysis (acid decomposition) (6N hydrochloric acid, 110° C., 24 hours): Glu: 2.00, Lys: 2.82 Elemental analysis (%) Calcd. for $C_{28}H_{52}N_8O_{10} \cdot CH_3COOH \cdot 5H_2O$: C, 44.43; H, 8.20; N, 13.81 Found: C. 45.08; H, 8.17; N, 13.76 $[\alpha]_D = -27.1°$ (c=0.14, water)

EXAMPLE 15

Production of H-Lys-Leu-Lys-Ser-Glu-OH:

(1) Boc-Leu-Lys(Z)-Ser(Bzl)-Glu(OBzl)OBzl→Z-Lys(Z)-Leu-Lys(Z)-Ser(Bzl)-Glu(OBzl)OBzl (1):

Boc-Leu-Lys(Z)-Ser(Bzl)-Glu(OBzl)OBzl (1.50 g) was treated with trifluoroacetic acid (15 ml) at room temperature for 30 minutes. After removal of the trifluoroacetic acid by distillation, the residue was powderized with isopropyl ether and the powder was dissolved in dry tetrahydrofuran (30 ml). The solution was cooled to 0° C., and N-methylmorpholine (0.15 g) and Z-Lys(Z)OSu (0.783 g) were added. The mixture was stirred at 0°-5° C. for 7 hours and allowed to stand at room temperature. The reaction mixture was concentrated to half its original volume, and ethyl acetate (150 ml) was added. The mixture was washed with 2% hydrochloric acid (50 ml), water (50 ml×2), 2% sodium hydrogen carbonate (50 ml) and water (50 ml×2) in that order and dried over magnesium sulfate. The solvent was then distilled off and the residue was crystallized from ether to give Z-Lys(Z)-Leu-Lys(Z)-Ser(Bzl)-Glu(OBzl)OBzl (1) (1.60 g).

mp: 160°-165° C. Elemental analysis (%) Calcd. for $C_{71}H_{85}N_7O_{15}$: C, 66.81; H, 6.71; N, 7.68 Found: C, 66.62; H, 6.60; N, 7.80 Thin layer chromatography: Rf=0.17 [solvent: ethyl acetate-chloroform (1:1), carrier: silica gel 60F254 (Merck)] $[\alpha]_D = -14.9°$ (c=0.11, dimethylformamide)

(2) Compound (1)→H-Lys-Leu-Lys-Ser-Glu-OH (2):

Z-Lys(Z)-Leu-Lys(Z)-Ser(Bzl)-Glu(OBzl)OBzl (1) (1.40 g) was treated with hydrogen fluoride (35 ml) in the presence of anisole (1.5 ml) at 0° C. for an hour. The hydrogen fluoride was distilled off and the residue was dissolved in water (40 ml). The solution was washed with ether (20 ml) and chromatographed on a Dowex 1×2 column (3.5×20 cm) (acetate form), elution being carried out with water. The ninhydrin-positive eluate fractions were combined, concentrated to 30 ml and lyophilized to give a crude powder (680 mg). This powder was dissolved in 0.05M pyridine-acetic acid buffer (pH 5.4) (10 ml) and the solution was subjected to chromatography using a CM cellulose column (2.7×54 cm) preliminary equilibrated with the same buffer. The column was eluted in the manner of linear concentration gradient elution with 0.05M-0.4M pyridine-acetic acid buffer (pH 5.4) (750 ml each). The main fractions were combined and lyophilized to give a powder (530 mg). This powder was dissolved in 0.5N acetic acid (5 ml) and the solution was chromatographed on a Sephadex G-15 column, followed by development with 0.5N acetic acid. The ninhydrin-positive eluate fractions were combined and lyophilized to give H-Lys-Leu-Lys-Ser-Glu-OH (2) (426 mg).

Amino acid analysis (acid decomposition) (6N hydrochloric acid, 110° C., 24 hours) Glu: 1.00, Leu: 1.00, Ser: 0.94, Lys: 1.86 Elemental analysis (%) Calcd. for $C_{26}H_{49}N_7O_9 \cdot CH_3COOH \cdot 3H_2O$: C, 46.85; H, 8.28; N, 13.65 Found: C, 46.27; H, 8.11; N, 13.58 Thin layer chromatography: Rf=0.71 [solvent: n-butanol-acetic acid-water-pyridine (2:2:2:1), carrier: cellulose] $[\alpha]_D = -24.7°$ (c=0.29, water)

EXAMPLE 16

Production of pGlu-Lys-Ala-Lys-Lys-Gln-Gly-Gly-Ser-Asn-OH:

(1) Resin→Boc-Gln-Gly-Gly-Ser(Bzl)-Asp-(resin)OBzl:

A solid-phase reactor was charged with benzhydrylamine resin (styrene-2% divinylbenzene copolymer) hydrochloride (0.4 mM/g) (8 g) and BocAspOBzl, Boc-Ser(Bzl)-OH, Boc-Gly-OH, Boc-Gly-OH, and Boc-Gln-OH were successively coupled in accordance with the under-mentioned schedule. The coupling reaction of Boc-Gln-OH was conducted in methylene chloride-dimethylformamide (1:1) in the presence of 1-hydroxybenztriazole.

| Schedule | | |
|---|---|---|
| Step | Reagent or solvent | Time (min) × number of runs |
| 1 (Washing) | Methylene chloride | 3 × 3 |
| 2 (Deprotection) | 50% (v/v) trifluoroacetic acid-methylene chloride | 30 × 1 |
| 3 (Washing) | Methylene chloride | 3 × 3 |
| 4 (Washing) | 2-Propanol | 3 × 2 |
| 5 (Washing) | Methylene chloride | 3 × 3 |
| 6 (Neutralization) | 5% (v/v) triethylamine-methylene chloride | 3 × 2 |
| 7 (Washing) | Methylene chloride | 3 × 3 |
| 8 (Coupling) | Each amino acid (3 moles) and dicyclohexylcarbodiimide (3 moles) in methylene chloride | 3-5 hr × 1 |
| 9 (Washing) | Methylene chloride | 3 × 5 |
| 10 (Washing) | 2-Propanol | 3 × 3 |

-continued

Schedule

| Step | Reagent or solvent | Time (min) × number of runs |
|---|---|---|
| 11 (Washing) | Dimethylformamide | 3 × 3 |

Note
The coupling reaction of Boc—Asp—Bzl started with Step 6. Unless otherwise stated, all reactions mentioned in the above schedule were conducted at room temperature.

After completion of reactions in accordance with the above schedule, the reaction product was washed with methanol and dried under reduced pressure to give Boc-Gln-Gly-Gly-Ser(Bzl)-Asp(resin)OBzl (10.16 g).

(2) 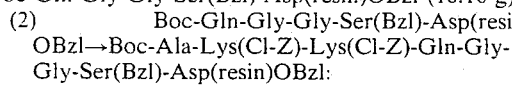

In accordance with the schedule indicated hereabove, Boc-Lys(Cl-Z)-OH, Boc-Lys(Cl-Z)-OH and Boc-Ala-OH were serially coupled to Boc-Gln-Gly-Gly-Ser(Bzl)-Asp(resin)OBzl (5.08 g). The commercial Boc-Lys(Cl-Z).t-butylamine salt was desalted before use. The reaction product was washed with methanol and dried under reduced pressure to give Boc-Ala-Lys(Cl-Z)-Lys-(Cl-Z)-Gln-Gly-Gly-Ser(Bzl)-Asp(resin)OBzl (6.09 g).

(3) 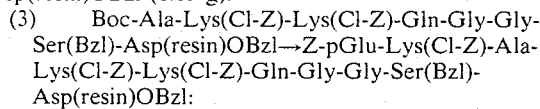

In accordance with the same schedule as above, Boc-Lys(Cl-Z)-OH and Z-pGlu-OH were successively coupled to Boc-Ala-Lys(Cl-Z)-Lys(Cl-Z)-Gln-Gly-Gly-Ser(Bzl)-Asp(resin)OBzl (3.05 g). The commercial Boc-Lys(Cl-Z).t-butylamine salt was desalted before use.

The reaction product was washed with methanol and dried under reduced pressure to give Z-pGlu-Lys(Cl-Z)-Ala-Lys(Cl-Z)-Lys(Cl-Z)-Gln-Gly-Gly-Ser(Bzl)-Asp(resin)OBzl (3.12 g).

Amino acid analysis (acid hydrolysis) [propionic acid-12N hydrochloric acid (1:1), 110° C., 24 hrs.] Asp: 1.0, Ser: 0.42, Glu: 1.63, Gly: 1.90, Ala: 0.86, Lys: 2.15.

(4) 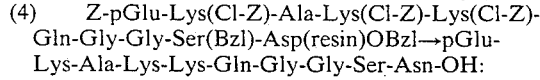

In the presence of anisole (5 ml), Z-pGlu-Lys(Cl-Z)-Ala-Lys(Cl-Z)-Lys(Cl-Z)-Gln-Gly-Gly-Ser(Bzl)-Asp(resin)OBzl (3.12 g) was treated with hydrogen fluoride (50 ml) at 0° C. for 1 hour. The hydrogen fluoride was distilled off under reduced pressure and the residue was extracted with water. The extract was washed with ether and passed through a Dowex 1×2 (acetate-form) column (200 ml), elution being carried out with water. Ninhydrin-positive fractions were pooled and lyophilized to give a crude product.

This crude product was chromatographed on a Whatman CM-52 column (3.2×65 cm) and elution is carried out by the linear gradient method using 0.4M to 1.0M pyridine-acetate buffer (pH 5.4) (1 l each). Main fractions were pooled and the solvent was distilled off under reduced pressure. The residue was chromatographed on a Sephadex LH-20 column (3.2×65 cm) using 0.2% acetic acid-water as the eluent. Fractions containing the desired product were pooled and lyophilized to give pGlu-Lys-Ala-Lys-Lys-Gln-Gly-Gly-Ser-Asn-OH as a pure product (359 mg).

Amino acid analysis (acid hydrolysis) (6N HCl, 110° C., 24 hours): Asp: 1.00, Ser: 0.79, Glu: 1.85, Gly: 1.86, Ala: 0.96, Lys: 2.69 Elemental analysis (%): $C_{42}H_{73}N_{15}O_{15}.10H_2O.CH_3COOH$ Calcd.: C, 41.67; H, 7.71; N, 16.57 Found: C, 42.04; H, 7.44; N, 16.12 Thin layer chromatography: Rf=0.44 [Solvent sytem: n-butanol-acetic acid-water-pyridine (2:2:2:1), cellulose plate, Merck No. 5552] High performance liquid chromatography: Pump: Waters 6000 A (Waters Associates) Column: Nucleosil 5 $C_{18}$ (150 mm×4 mm) Eluent: 0.1M phosphoric acid-dipotassium hydrogen phosphate buffer (pH 4.5) Flow rate: 1.0 ml/min. Detection: UV 210 nm Retention time: 7.05 min. $[\alpha]_D = -58.9°$ (c=0.514, water)

EXAMPLE 17

Production of pGlu-Ala-Lys-Lys-Gln-Gly-Gly-Ser-Asn-OH:

(1) 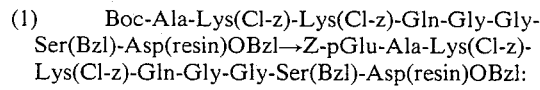

In accordance with the same schedule as Example 16 (1), Z-pGlu-OH was coupled to Boc-Ala-Lys(Cl-Z)-Lys(Cl-Z)-Gln-Gly-Gly-Ser(Bzl)-Asp(resin)OBzl (3.05 g). (The resin was the same as that used in Example 16.) After completion of the reaction, the product was washed with methaonl and dried under reduced pressure to give Z-pGlu-Ala-Lys(Cl-z)-Lys(Cl-z)-Gln-Gly-Gly-Ser(Bzl)-Asp(resin)OBzl (3.1 g).

Amino acid analysis (acid hydrolysis) [propionic acid-12N HCl (1:1), 110° C., 24 hrs.]: Asp: 1.00, Ser: 0.43, Glu: 1.71, Gly: 1.90, Ala: 0.88, Lys: 1.49.

(2) 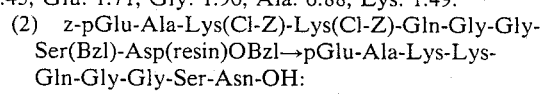

Z-pGlu-Ala-Lys(Cl-z)-Lys(Cl-z)-Gln-Gly-Gly-Ser(Bzl)-Asp(resin)OBzl (3.08 g) was treated substantially in the same manner as Example 16-(4) to give pGlu-Ala-Lys-Lys-Gln-Gly-Gly-Ser-Asn-OH (464 mg).

Amino acid analysis (acid hydrolysis) (6N HCl, 110° C., 24 hrs.): Asp: 1.00, Ser: 0.84, Glu: 1.92, Gly: 1.90, Ala: 0.87, Lys: 1.86 Elemental analysis (%): $C_{36}H_{61}N_{13}O_{14}.5H_2O.CH_3COOH$ Calcd.: C, 43.46; H, 7.20; N, 17.34 Found: C, 43.42; H, 7.43; N, 17.38 Thin layer chromatography: Rf=0.16 [solvent system: n-butanol-acetic acid-water-pyridine (3:1:2:1), cellulose plate, Merck No. 5552] High performance liquid chromatography: Pump: Waters 6000 A (Waters Associates) Column: Nucleosil 5 $C_{18}$ (150 mm×4 mm) Eluent: 0.1M phosphoric acid-dipotassium hydrogen phosphate buffer (pH 2.5) Flow rate: 1.0 ml/min. Detection: UV 210 nm Retention time: 5.3 min. $[\alpha]_D = -65.0°$ C. (c=0.51, water)

EXAMPLE 18

Production of pGlu-Lys-Ala-Lys-Ser-Gln-Gly-Gly-Ser-Asn-OH:

(1) 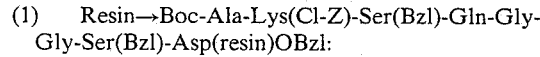

A solid-phase reactor was charged with benzhydrylamine resin hydrochloride (0.4 mM/g) styrene-2% divinylbenzene copolymer) (3.0 g), and in accordance with the schedule given in Example 16-(1) Boc-AspOBzl, Boc-Ser(Bzl)-OH, Boc-Gly-OH, Boc-Gly-OH, Boc-Gln-OH, Boc-Ser(Bzl)-OH, Boc-Lys(Cl-Z)-OH and Boc-Ala-OH were sequentially coupled.

After completion of the reactions, the product was washed with methanol and dried under reduced pressure to give Boc-Ala-Lys(Cl-Z)-Ser(Bzl)-Gln-Gly-Gly-Ser(Bzl)-Asp(resin)OBzl (4.138 g).

(2) Boc-Ala-Lys(Cl-z)-Ser(Bzl)-Gln-Gly-Gly-Ser(Bzl)-Asp(resin)-OBzl→Z-pGlu-Lys(Cl-Z)-Ala-Lys(Cl-z)-Ser-(Bzl)-Gln-Gly-Gly-Ser(Bzl)-Asp(resin)-OBzl:

To Boc-Ala-Lys(Cl-z)-Ser(Bzl)-Gln-Gly-Gly-Ser(Bzl)-Asp(resin)OBzl (2.069 g) as a starting material, there were coupled Boc-Lys(Cl-Z)-OH and Z-pGlu-OH in that order in accordance with the schedule of Example 16-(1). After completion of the reactinos, the product was washed with methanol and dried under reduced pressure to give Z-pGlu-Lys(Cl-z)-Ala-Lys(Cl-z)-Ser(Bzl)-Gln-Gly-Gly-Ser(Bzl)-Asp(resin)OBzl (2.12 g).

Amino acid analysis (acid hydrolysis) [Propionic acid-12N HCl (1:1), 110° C., 24 hrs.] Asp: 1.12, Ser: 0.31, Glu: 1.90, Gly: 2.00, Ala: 1.00, Lys: 1.73

(3) Z-pGlu-Lys(Cl-Z)-Ala-Lys(Cl-Z)-Ser(Bzl)-Gln-Gly-Gly-Ser(Bzl)-Asp(resin)OBzl→pGlu-Lys-Ala-Lys-Ser-Gln-Gly-Gly-Ser-Asn-OH:

In the presence of anisole (2 ml), Z-pGlu-Lys(Cl-z)-Ala-Lys(Cl-z)-Ser(Bzl)-Gln-Gly-Gly-Ser(Bzl)-Asp(resin)OBzl (2.12 g) was treated with hydrogen fluoride (30 ml) at 0° C. for 1 hour. The hydrogen fluoride was distilled off under reduced pressure and the residue was extracted with water. The extract was washed with ether and passed through an IR-45 (acetate-form) (200 ml) column, elution being carried out with water. Ninhydrin-positive fractions were pooled and lyophilized. The lyophilisate was applied to a Watman CM-25 column (2.5 cm×50 cm) column equilibriated with 0.1M pyridine-acetate buffer (pH 5.4), and elution was carried out by the linear gradient method using 0.1 through 0.4M pyridine-acetate buffer (pH 5.4) (500 ml each). Main fractions were pooled and lyophilized. This lyophilisate was passed throgh a Sephadex LH-20 column (3.2 cm×65 cm, 0.2% acetic acid) and main fractions were pooled and lyophilized to obtain pGlu-Lys-Ala-Lys-Ser-Gln-Gly-Gly-Ser-Asn-OH as a pure product (185 mg).

Amino acid analysis (acid hydrolysis) (6N HCl, 110° C., 24 hrs.) Asp: 1.00, Ser: 1.62, Glu: 1.90, Gly: 1.88, Ala: 1.00, Lys: 1.86 Elemental analysis (%): $C_{39}H_{65}N_{14}O_{16}.9H_2O.CH_3COOH$ Calcd.: C, 40.76; H, 7.26; N, 16.23 Found: C, 41.45; H, 7.08; N, 16.31 Thin layer chromatography: Rf=0.14 [solvent system: chloroform-methanolaqueous ammonia (2:2:1); silica gel plate Merck No. 5714] High performance liquid chromatography: Pump: Waters 6000A (Waters Associates) Column: Nucleosil 5 $C_{18}$ (150 mm×4 mm) Eluent: 0.1M phosphoric acid-dipotassium hydrogen phosphate buffer (pH 4.5) Flow rate: 1.0 ml/min. Detection: UV 210 nm Retention time: 7.0 min. $[\alpha]_D = -58.69°$ (c=0.51, water)

We claim:

1. A peptide, wherein the peptide is represented by the following formula: H-Lys-Leu-Lys-Ser-Glu-OH and its pharmaceutically acceptable salt.

2. A peptide selected from the group consisting of a peptide of the following formulae: H-Thr-Lys-Glu-Lys-Leu-Lys-Ser-Glu-Leu-Val-Ala-Asn-OH, H-Glu-Lys-Leu-Lys-Ser-Glu-Leu-Val-Ala-Asn-OH, H-Lys-Leu-Lys-Ser-Glu-OH, and a pharmaceutically acceptable salt thereof.

3. A pharmaceutical composition for immunopotentiation comprising, as an active ingredient, an effective amount of a peptide as defined in claim 2 or a pharmaceutically acceptable salt thereof and a nontoxic, pharmaceutically acceptable vehicle or carrier.

4. A method of use of a peptide as defined in claim 2 and pharmaceutically acceptable salt thereof for therapeutic treatment of infectious diseases caused by bacteria or virus which comprises administering to the host of said infectious disease an effective immunopotentiating amount of the peptide.

* * * * *